(12) United States Patent
Fujioka et al.

(10) Patent No.: US 8,696,634 B2
(45) Date of Patent: Apr. 15, 2014

(54) SYRINGE DRIVE DEVICE

(75) Inventors: Soichiro Fujioka, Osaka (JP); Tohru Nakamura, Osaka (JP); Osamu Mizuno, Osaka (JP); Akinobu Okuda, Nara (JP); Akihiro Ohta, Osaka (JP); Mizuho Sakakibara, Tokyo (JP); Toshihide Ueda, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/575,124

(22) PCT Filed: Jan. 26, 2011

(86) PCT No.: PCT/JP2011/000404
§ 371 (c)(1),
(2), (4) Date: Jul. 25, 2012

(87) PCT Pub. No.: WO2011/093064
PCT Pub. Date: Aug. 4, 2011

(65) Prior Publication Data
US 2012/0330237 A1 Dec. 27, 2012

(30) Foreign Application Priority Data
Jan. 27, 2010 (JP) ................................. 2010-014974

(51) Int. Cl.
*A61M 37/00* (2006.01)
(52) U.S. Cl.
USPC ......................................... 604/154; 604/131
(58) Field of Classification Search
USPC .................................................. 604/131, 154
See application file for complete search history.

(56) References Cited

U.S. PATENT DOCUMENTS

| 6,270,473 B1 | 8/2001 | Schwebel |
| 2004/0057854 A1 | 3/2004 | Wakabayashi et al. |
| 2004/0122369 A1 | 6/2004 | Schriver et al. |

FOREIGN PATENT DOCUMENTS

| JP | 3-247347 | 11/1991 |
| JP | 2004-73373 | 3/2004 |

(Continued)

OTHER PUBLICATIONS

International Search Report issued Mar. 22, 2011 in International (PCT) Application No. PCT/JP2011/000404.

(Continued)

*Primary Examiner* — Victoria P Shumate
(74) *Attorney, Agent, or Firm* — Wenderoth, Lind & Ponack, L.L.P.

(57) ABSTRACT

A syringe drive device 15 according to the present invention includes: an outer tube fixing portion 31 that detachably fixes an outer tube 22 of a syringe 16; a plunger holder 21 that holds a plunger 17 of the syringe 16; and a drive portion that moves the plunger holder 21 along an axis of the syringe. The outer tube fixing portion 31 includes: a flange catcher 33 facing a rear end of a flange 22a of the outer tube 22, the rear end being located far from the plunger 17 to be pushed; slide portions 34 and 35 that are located in front of a front end of the flange 22a to hold the flange 22a between the flange catcher 33 and the slide portions, the front end being located close to the plunger 17 to be pushed; slide guides 36 and 37 that support the slide portions 34 and 35 so as to be slidable along the axis of the syringe; and a slide portion operation mechanism that is switchable between a first state where the slide portions 34 and 35 slide along the axis of the syringe, and a second state where the slide portions 34 and 35 are held at positions to hold the flange 22a between the flange catcher 33 and the slide portions.

9 Claims, 22 Drawing Sheets

(56) References Cited

FOREIGN PATENT DOCUMENTS

| JP | 2004-305361 | 11/2004 |
| JP | 2005-52367 | 3/2005 |
| JP | 2006-510450 | 3/2006 |

OTHER PUBLICATIONS

English translation International Preliminary Report issued Sep. 18, 2012 in International (PCT) Application No. PCT/JP2011/000404.

---------- RELEASED STATE

—--—--— DURING DEFORMATION

Fig. 7
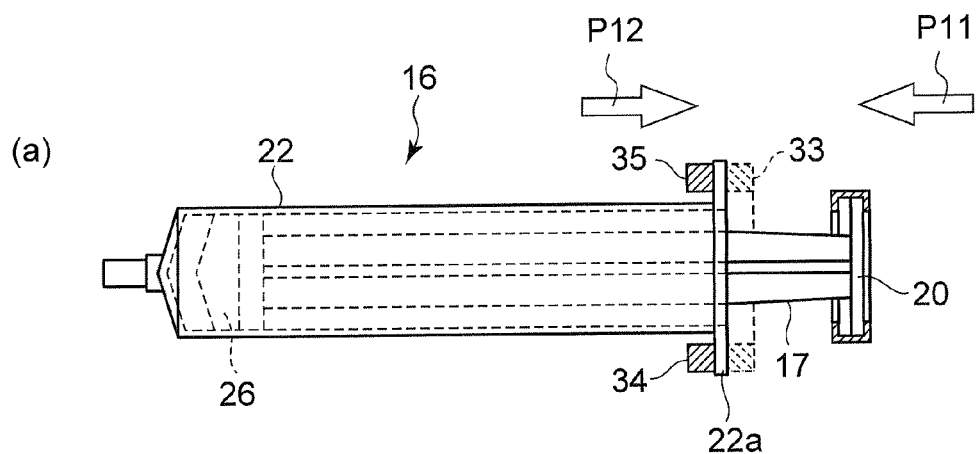
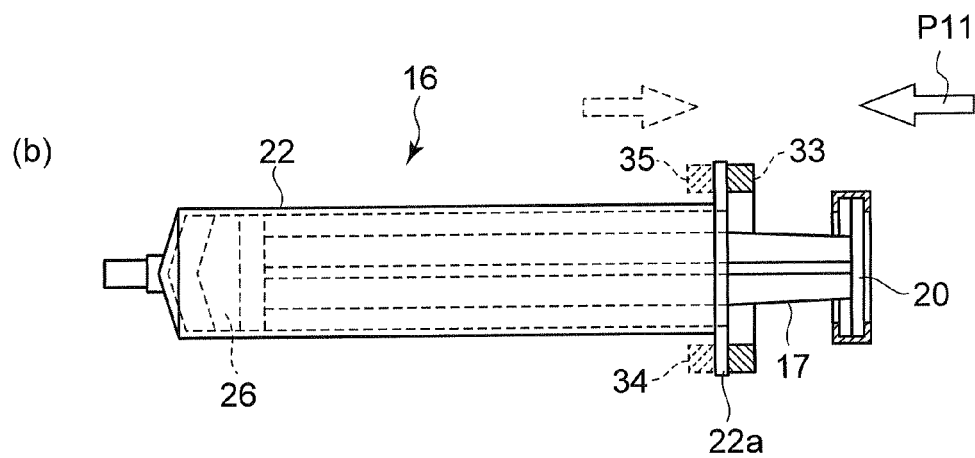

Fig.11
(a) 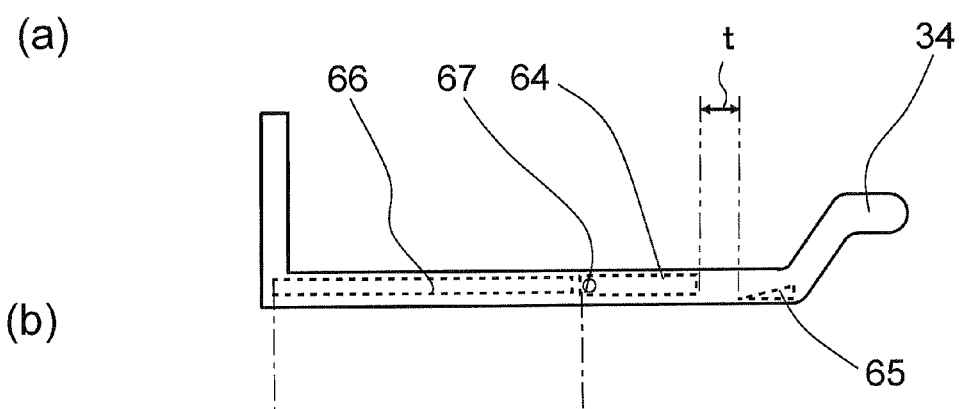
(b) 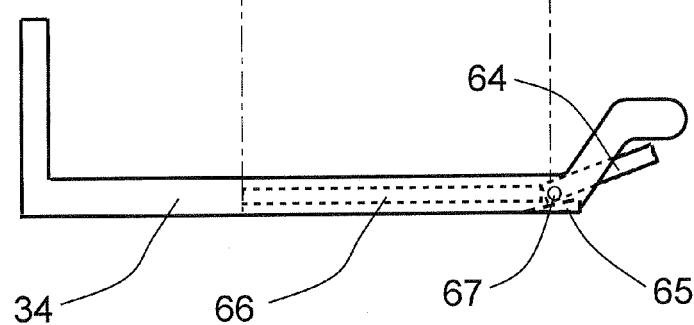

Fig.12
(a)
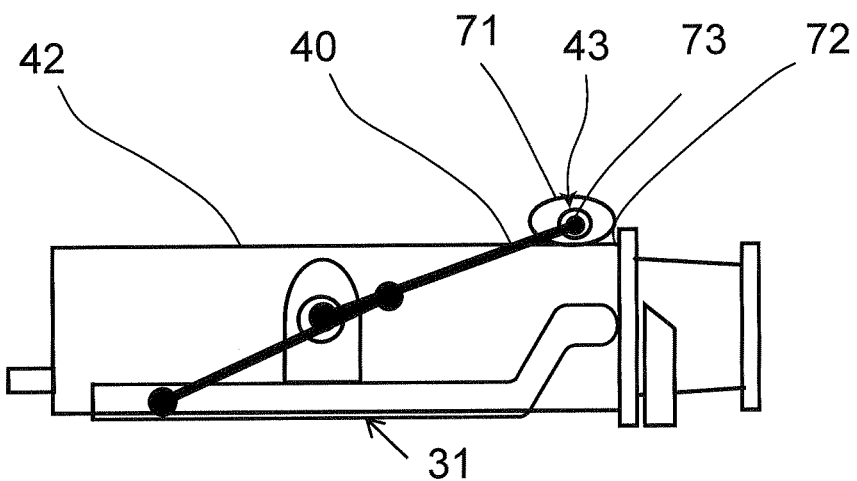
(b)
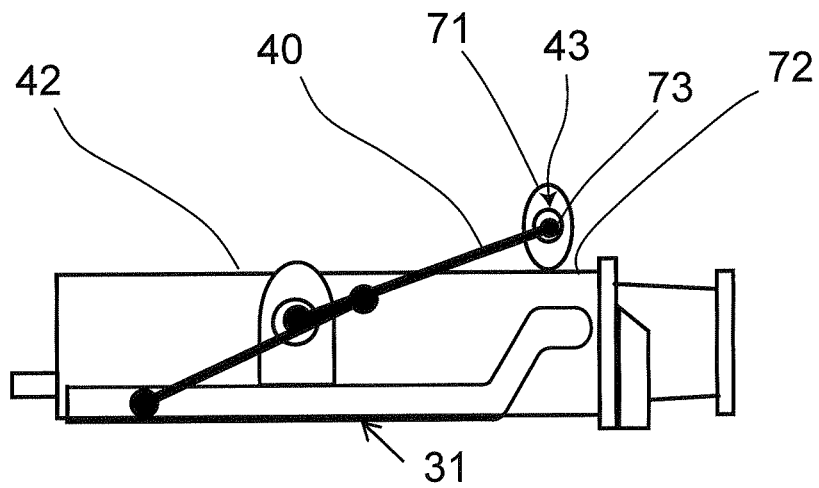

Fig. 22
(a) PRIOR ART
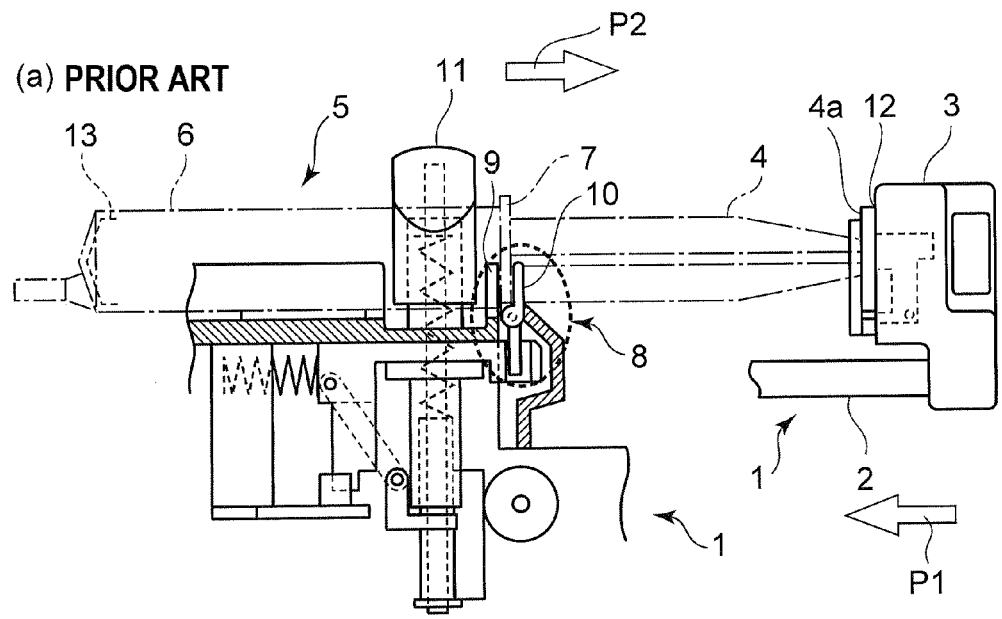
(b) PRIOR ART
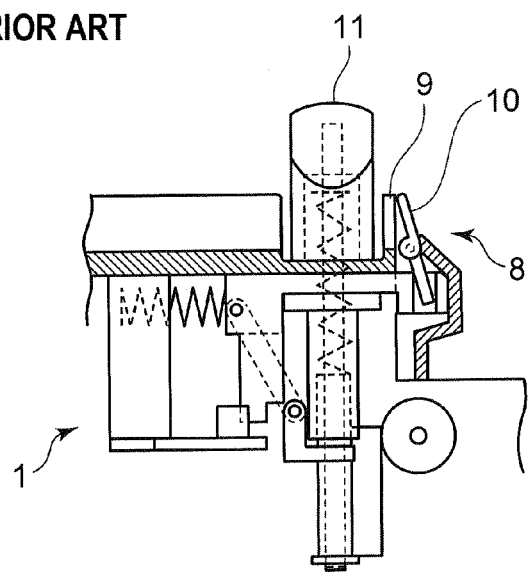

SYRINGE DRIVE DEVICE

TECHNICAL FIELD

The present invention relates to a syringe that is used for mixing medicinal solutions, etc. The present invention particularly relates to a syringe drive device that assists in pushing and pulling a plunger with respect to a syringe.

BACKGROUND ART

In the operation of mixing medicinal solutions, the medicinal solution in a vial is manually aspirated into a syringe to discharge the medicinal solution in the syringe. When medicinal solutions are mixed in a hospital, a plurality of operations are often performed at one time. Accordingly, it is quite a workload for a mixing person to push and pull a plunger with respect to a syringe in order to mix the medicinal solutions. For the purpose of reducing the workload of the mixing person, it has been considered a syringe drive device, which causes a plunger to be pushed and pulled by drive power of a motor.

There is a syringe drive device (infusion solution transfer device) that causes a plunger to be pushed by drive power of a motor, although it is not a device used in mixing operations (refer to JP 2004-73373 A).

FIG. 22(a) is a sectional view showing a main portion of an infusion solution transfer device 1 disclosed in JP 2004-73373 A, in a state where a syringe is attached. By moving a drive shaft 2 that is coupled to a drive mechanism such as a motor, a plunger holder 3 is linearly moved. When the plunger holder 3 pushes the plunger 4, a medicinal solution in a syringe 5 is discharged from an injection port.

The infusion solution transfer device 1 includes a flange attachment 8 used for fixing a flange 7 of an outer tube 6 of the syringe 5. The flange attachment 8 has a flange front surface support portion 9 which is fixed, and a flange rear portion presser plate 10 which is movable, so that the flange 7 having a different thickness can be fixed reliably. FIG. 22(b) is a sectional view showing a main portion of the infusion solution transfer device 1 in a state where the syringe 5 is not attached. When a knob 11 is operated, the flange rear portion presser plate 10 is rotated and can move close to and away from the flange front surface support portion 9. Therefore, the flange rear portion presser plate 10 can push the flange 7 having a different thickness against the flange front surface support portion 9.

The infusion solution transfer device 1 (syringe drive device) thus configured has a problem that, after the plunger 4 is pushed toward the outer tube 6, the syringe 5 is held between the flange front surface support portion 9 and a press surface 12 of the plunger holder 3, with a result that the syringe 5 cannot be easily detached.

The syringe 5 is held for the following reason. When the plunger 4 is pushed by the plunger holder 3, the outer tube 6 is frictioned with a gasket that is provided at a distal end of the plunger 4. Accordingly, as indicated by an arrow P1 in FIG. 22(a), the outer tube 6 tends to move forward (toward the injection port of the syringe 5) together with the plunger 4. On the other hand, as indicated by an arrow P2 in FIG. 22(a), the flange front surface support portion 9 prevents the forward movement of the flange 7 against the force (arrow P1) of the plunger holder 3 to push forward the plunger 4. In other words, the flange front surface support portion 9 and the press surface 12 of the plunger holder 3 press the flange 7 of the syringe and a brim 4a of the plunger 4 in directions opposite to each other. As a result, the syringe 5 is held between the flange front surface support portion 9 and the press surface 12 of the plunger holder 3.

Particularly in a state where the plunger 4 is pushed to the limit (a state where the gasket provided at the distal end of the plunger 4 is in contact with a front wall surface 13 of the outer tube 6), the syringe 5 is rigidly held by the force of the plunger holder 3 to push the plunger 4. Accordingly, it is more difficult to detach the syringe 5 in this state.

Further, in this infusion solution transfer device 1, the flange 7 is held between the flange front surface support portion 9 and the flange rear portion presser plate 10 to fix the syringe 5. Thus, the syringe 5 is fixed only in the axial direction thereof, and the syringe 5 is not sufficiently fixed in the detached direction.

SUMMARY OF THE INVENTION

The present invention has been made to solve these problems, and an object thereof is to provide a syringe drive device that allows a syringe to be easily attached and detached, as well as can stably fix the syringe.

In order to achieve this object, according to the present invention, a syringe drive device includes: an outer tube fixing portion detachably fixing an outer tube of a syringe; a plunger holder holding a plunger of the syringe; and a drive portion moving the plunger holder along an axis of the syringe; the plunger being pushed or pulled along the axis of the syringe by moving the plunger holder; wherein the outer tube fixing portion includes: a flange catcher facing a rear end of a flange of the outer tube, the rear end being located far from the plunger to be pushed; a slide portion located in front of a front end of the flange to hold the flange between the flange catcher and the slide portion, the front end being located close to the plunger to be pushed; a slide guide supporting the slide portion so as to be slidable along the axis of the syringe; and a slide portion operation mechanism being switchable between a first state where the slide portion slides along the axis of the syringe, and a second state where the slide portion is held at a position to hold the flange between the flange catcher and the slide portion.

The syringe drive device according to the present invention can stably fix a syringe, while the syringe is not held and thus can be easily attached and detached.

BRIEF DESCRIPTION OF THE DRAWINGS

FIG. 6(a) is a schematic view showing the attached state, FIG. 6(b) is a schematic view showing a state at an inflection point, and FIG. 6(c) is a schematic view showing a state where a fixed support is positioned below an inflection line.

FIGS. 7(a) and 7(b) are pattern views illustrating prevention of holding in the embodiment 1; FIG. 7(a) shows a conventional syringe drive device that causes holding, and FIG. 7(b) is the syringe drive device according to the embodiment 1 which does not cause holding.

FIGS. 11(a) and 11(b) are views showing a relationship between a slide portion and a push-up portion according to the embodiment 1; FIG. 11(a) is a side view showing the attached state, and FIG. 11(b) is a side view showing the released state.

FIGS. 12(a) and 12(b) are schematic views of an outer tube fixing portion according to an embodiment 2 of the present invention; FIG. 12(a) is a side schematic view showing a state where a press portion being used is thin, and FIG. 12(b) is a side schematic view showing a state where the press portion being used is thick.

FIG. 13(a) is a side view of the slide portion, and FIG. 13(b) is a top view of the slide portion.

FIGS. 22(a) and 22(b) are views of a conventional infusion solution transfer device; FIG. 22(a) is a sectional view of a main portion in a state where a syringe is attached, and FIG. 22(b) is a sectional view of the main portion in a state where the syringe is not attached.

DESCRIPTION OF THE EMBODIMENTS

Embodiments of the present invention are described below with reference to the drawings. It is noted that the same components are denoted by the same reference signs, and description thereof will not be repetitively provided where appropriate.

Embodiment 1

Figure 1:
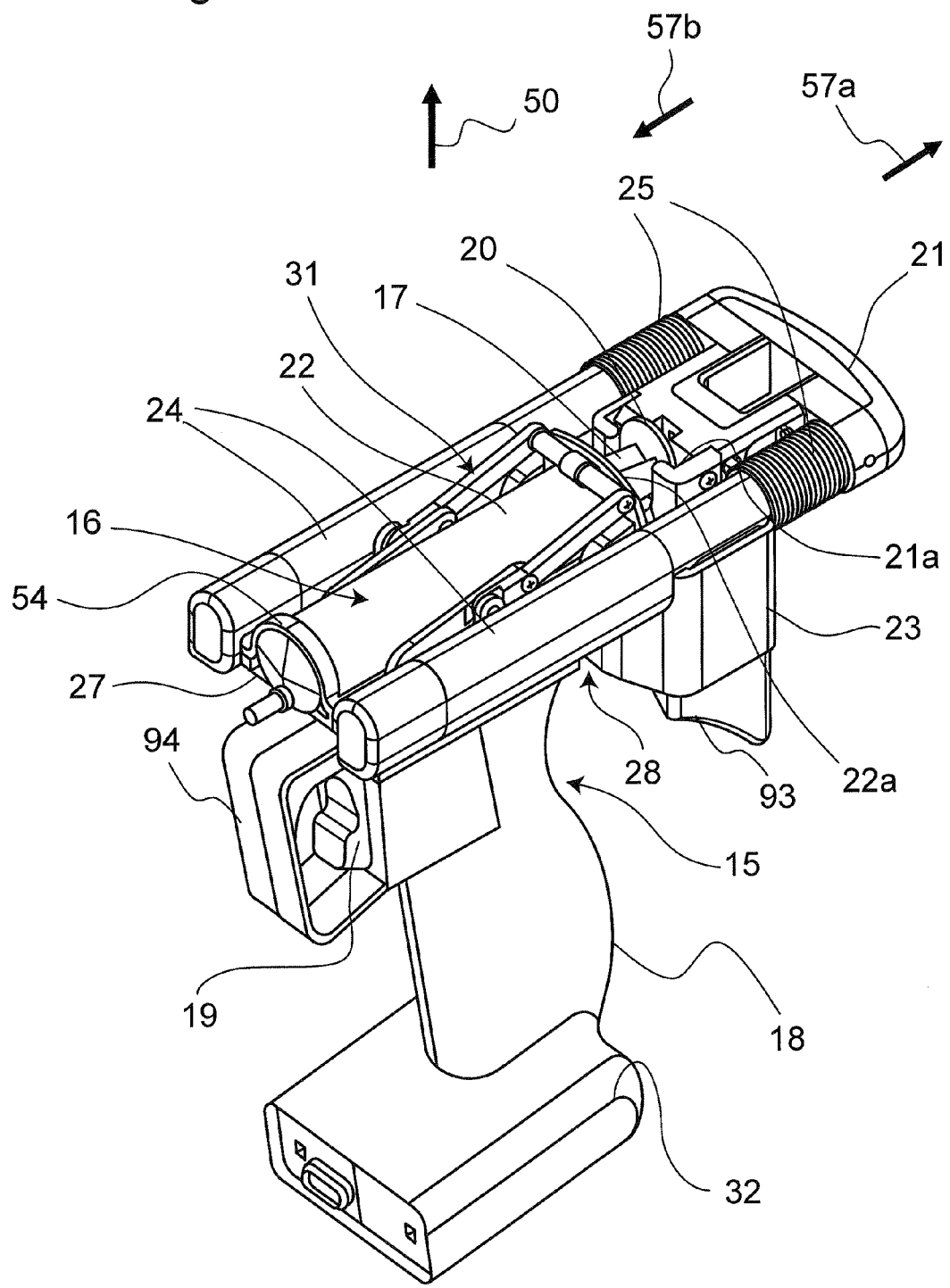
FIG. 1 is a perspective view of a syringe drive device according to an embodiment 1 of the present invention.

FIG. 1 is a perspective view of a syringe drive device according to the present embodiment 1. A syringe drive device 15 is a tool assisting in pushing and pulling a plunger 17 with respect to a syringe 16.

As shown in FIGS. 7(a) and 7(b), the syringe 16 includes an outer tube 22 having a distal end to which an injection needle 90 (see FIG. 21) is attached, and the plunger 17 having a distal end that is provided with a gasket 26 and is inserted into the outer tube 22 from an opening located far from the injection needle 90. The outer tube 22 has an open end provided with a flange portion 22a, and the plunger 17 has a rear end provided with a brim 20. In the following description, unless otherwise specified, a "front portion", a "front surface", and a "front end" each indicate a position at the distal end relative to the plunger (closest to the injection needle 90; in other words, the end toward which the plunger 17 is pushed and closest to where the material in the syringe is discharged) of the syringe 16. On the other hand, unless otherwise specified, a "rear portion", a "rear surface", and a "rear end" each indicate a position at the proximate end (farthest from the injection needle 90; in other words, the end toward which the plunger 17 is pulled and farthest from where the material in the syringe is discharged) of the syringe 16.

Figure 2:
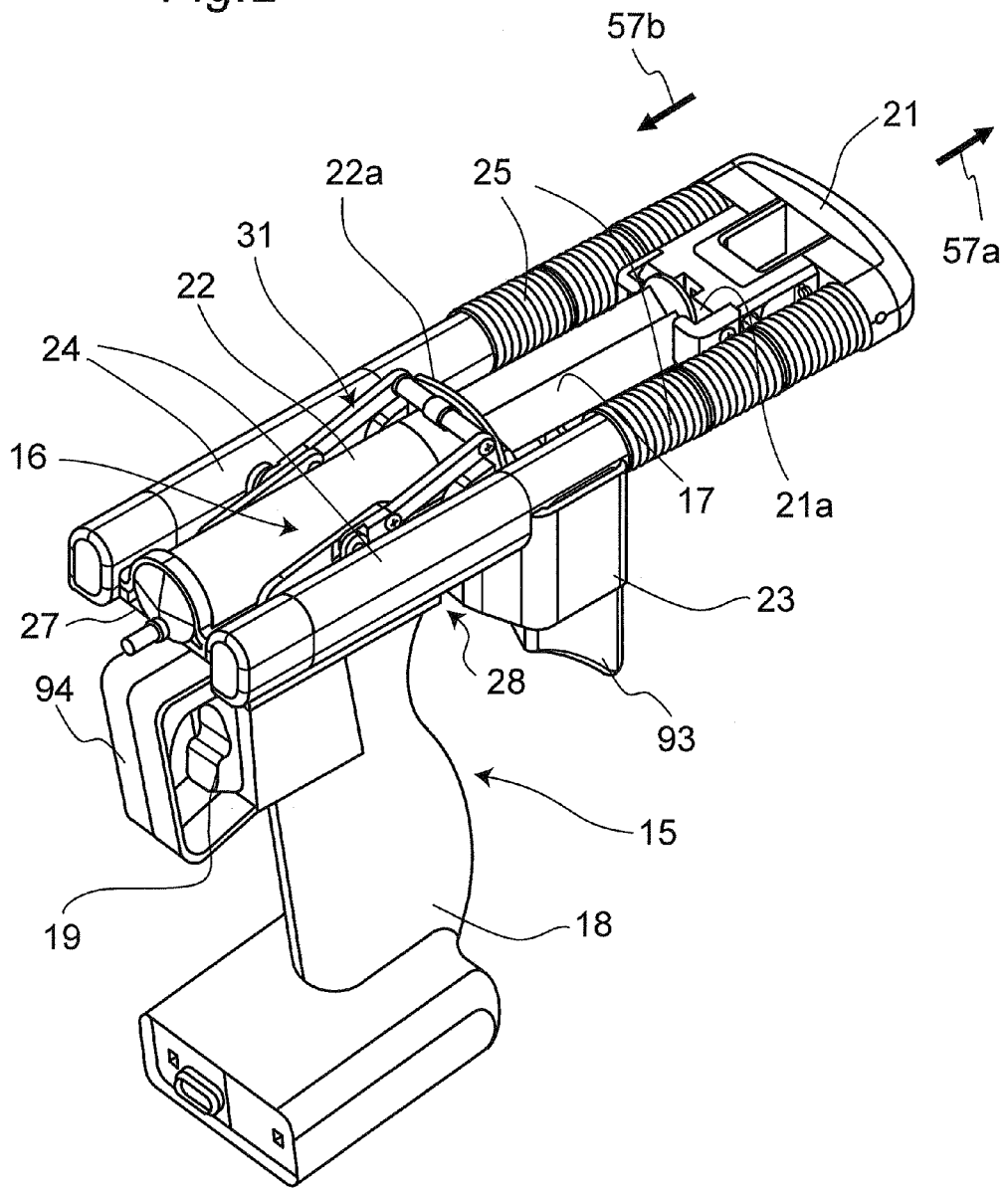
FIG. 2 is a perspective view of the syringe drive device according to the embodiment 1 in an extended state.

As shown in FIGS. 1 and 2, the syringe drive device 15 includes a main body 27 provided on the top thereof with an outer tube fixing portion 31 that fixes the outer tube 22 of the syringe 16, and a grip portion 18 that extends from a lower end of the main body 27. This grip portion 18 extends substantially perpendicularly to the longitudinal direction (along an axis of the syringe) of the outer tube 22 that is fixed to the outer tube fixing portion 31. The grip portion 18 has a sufficient size to allow an operator to hold the device with one hand. It is noted that the syringe drive device 15 according to the present embodiment 1 is of a handy cordless type inclusive of a battery portion 32 at a lower end of the grip portion 18.

The syringe drive device 15 further includes a plunger holder 21 that holds the plunger 17, and a plunger drive portion 28 that moves the plunger holder 21 along the axis of the syringe. The plunger holder 21 has an accommodating portion 21a that detachably accommodates the brim 20 of the plunger 17. The plunger drive portion 28 has a motor and a conversion gear (both not shown) that are mounted in a power converter 23 provided at a rear bottom of the main body 27. Rotation of the motor is transmitted, by way of the conversion gear, to paired racks (not shown) which are located at the respective ends of the syringe 16. Rear ends of these racks are coupled to the plunger holder 21, and therefore the plunger holder 21 moves in a direction corresponding to the direction of rotation of the motor. When the plunger holder 21 is moved along the axis of the syringe, the plunger 17 is pushed and pulled with respect to the fixed syringe 16.

The racks (not shown) of the plunger drive portion 28 are covered with rack covers 24 and stretchable covers 25, so that oil and the like adhering to the racks are prevented from spattering outward. These rack covers 24 and the stretchable covers 25 also prevent outside dirt from adhering to the racks. Moreover, the racks are protected from water by the rack covers 24 and the stretchable covers 25. Therefore, it is easy to wash the syringe drive device 15 according to the present embodiment 1.

The syringe drive device 15 includes an operation switch 19 that is located at an operable position when the grip portion 18 is held (on the front surface of the grip portion 18), and is used for operating the plunger drive portion 28. The operation switch 19 is structured in such a manner that an upper portion projects from a lower portion, thereby realizing intuitive operations. The operation switch 19, which has a projection at either one of the upper and lower portions, allows intuitive recognition upon touching the switch, with regard to which end is the upper portion (or the lower portion). Further, the operation switch 19 has, in front thereof, a trigger guard 94 having a ring shape. The trigger guard 94 is provided integrally with the grip portion 18. The trigger guard 94 is located so as to surround the operation switch 19 with a space being provided to allow a finger to be inserted thereinto. Further, in the syringe drive device 15, the power converter 23 is provided, at a lower end thereof, with a pad 93 that is configured by a rubber member or the like. This pad 93 is provided in order to soften a surface to be in contact with the back of a hand when the weight of the plunger drive portion 28 is received by the back of the hand. Accordingly, the pad 93 may be configured by a soft member having certain elasticity, in place of the rubber member.

Described below is the flow of the operation of mixing medicinal solutions. Firstly, an operator attaches the syringe 16 to the syringe drive device 15. The operator holds the grip portion 18 of the syringe drive device 15 with the right hand, for example, and places the index finger of the right hand holding the grip portion on the operation switch 19.

In the syringe drive device 15 according to the present embodiment 1, when the upper portion of the operation switch 19 is pressed, the motor of the plunger drive portion 28 rotates in the positive direction. This rotation of the motor is converted by the conversion gear into linear motion toward the rear ends of the racks. Then, the plunger holder 21, which holds the brim 20 of the plunger 17 in the accommodating portion 21a, is moved backward (along an arrow 57a) so as to be away from the outer tube 22 of the syringe 16. The plunger 17 is thus pulled out of the outer tube 22. As a result, as shown in FIG. 2, the plunger drive portion 28 is brought into the extended state where the racks largely project backward from the rack covers 24, respectively.

On the other hand, when the lower portion of the operation switch 19 is pressed, the motor of the plunger drive portion 28 rotates in the negative direction. This rotation of the motor is converted by the conversion gear into linear motion toward the front ends of the racks. Then, the plunger holder 21 is moved forward (along an arrow 57b) so as to come close to the flange 22a of the outer tube 22. The plunger 17 is thus pushed toward the outer tube 22. As a result, as shown in FIG. 1, the plunger drive portion 28 is brought into a state where the racks are mostly accommodated in the rack covers 24, respectively.

In this manner, the operator assists in pulling and pushing the plunger 17 with respect to the syringe 16 by pressing the upper portion and the lower portion of the operation switch 19, respectively. When the operation switch 19 is made flat (the state where none of the upper portion and the lower portion of the operation switch 19 is pressed), the plunger holder 21 stops moving.

Figure 21:
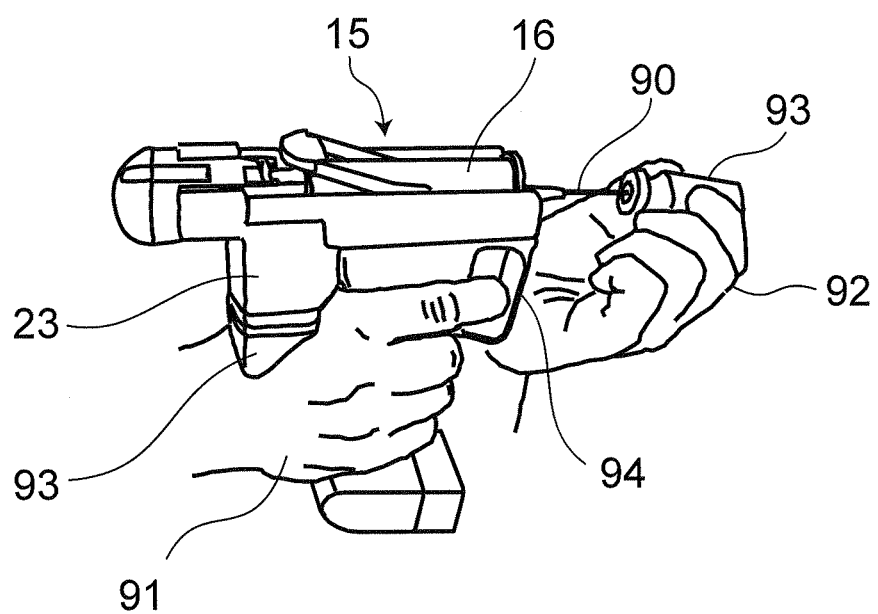
FIG. 21 is a pattern view showing a state where the syringe drive device according to the embodiment 1 of the present invention is used.

FIG. 21 is a pattern view showing an exemplary state where the syringe drive device 15 is used. This figure shows the state where the syringe drive device 15, to which the syringe 16 provided with the injection needle 90 is attached, is held with a right hand 91, and a medicinal solution is aspirated out of a vial 93 held with a left hand 92. If the trigger guard 94 of the syringe drive device 15 is pressed against the heel or the vicinity of the palm of the left hand 92, it is possible to stably keep the posture upon inserting the tip of the injection needle 90 into the vial 93. Therefore, accidents such as hurting with the needle can be effectively prevented. Further, it is possible to prevent erroneous operations of the operation switch 19, which may occur when the operation switch 19 or the index finger in contact with the operation switch 19 touches an obstacle or the like. The pad 93 is located so as to be in contact with the back of the hand in the region from the bases of the thumb and the index finger to the wrist of the right hand 91, which holds the grip portion. In this configuration, the weight of the syringe drive device 15 can be partially received by the back of the hand. Therefore, the operator can hold the syringe drive device 15 stably with a good balance, which enhances the safety in the operation.

The syringe drive device 15 further includes a syringe fixing mechanism (the outer tube fixing portion 31) which can stably fix the syringe 16 while the syringe 16 can be easily attached and detached. In order to describe the syringe fixing mechanism, the mechanisms of the syringe drive device 15 are referred to first.

Figure 3:
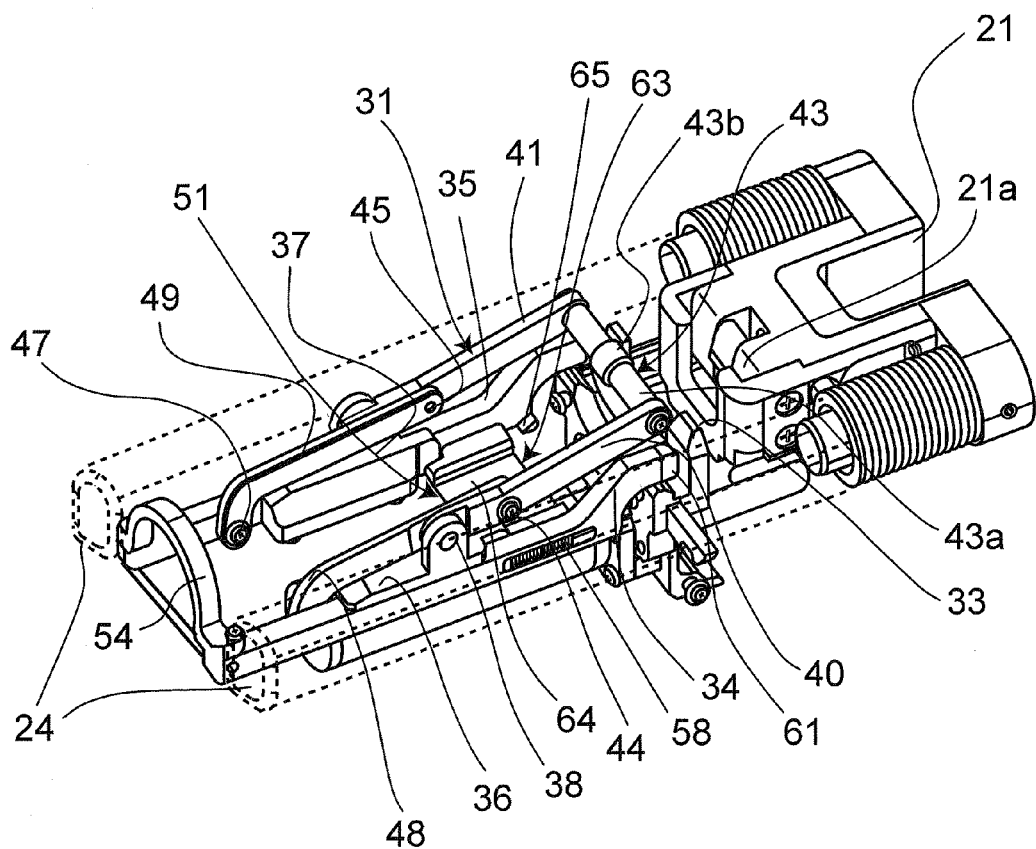
FIG. 3 is a perspective view showing a main portion of the syringe drive device according to the embodiment 1 in an attached state.
Figure 4:
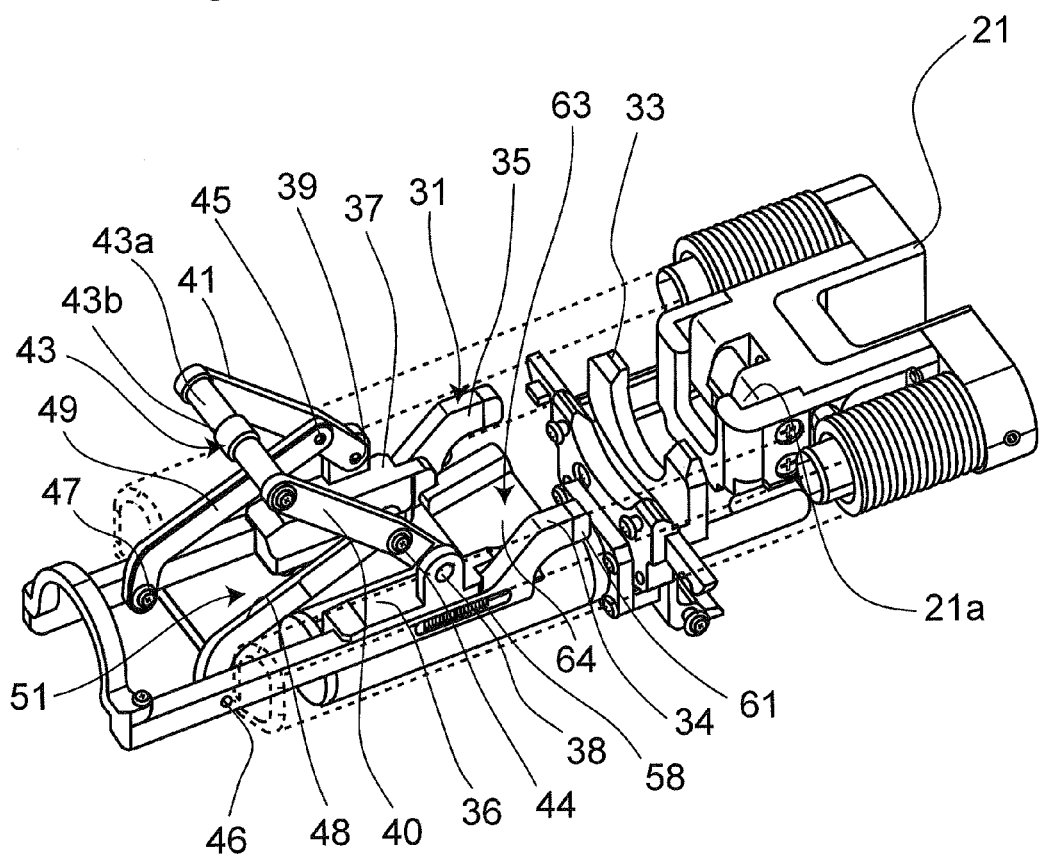
FIG. 4 is a perspective view showing the main portion of the syringe drive device according to the embodiment 1 in a released state.

FIG. 3 is a perspective view showing a main portion of the syringe drive device 15 in an attached state where the syringe 16 is fixed to the outer tube fixing portion 31. FIG. 4 is a perspective view showing the main portion of the syringe drive device 15 in a released state where the syringe 16 can be inserted into and extracted from the outer tube fixing portion 31. To be exact, FIG. 3 shows the state where the syringe 16 is fixed. However, for the purpose of understanding easily the internal structure, this figure does not show the syringe 16.

The outer tube fixing portion 31 has a syringe mount portion 51. The syringe mount portion 51 is configured as a space in which the outer tube 22 of the syringe 16 is mounted, when the syringe 16 is placed on the top of the main body 27 of the syringe drive device 15. The outer tube fixing portion 31 further includes a flange catcher 33, slide portions 34 and 35, and slide guides 36 and 37. The flange catcher 33 is located to face the rear end of the flange 22a of the outer tube 22 that is mounted in the syringe mount portion 51. The slide portions 34 and 35 are located in front of the flange 22a that is mounted in the syringe mount portion 51, so as to hold the flange 22a between the flange catcher 33 and the slide portions 34 and 35. The slide guides 36 and 37 hold the slide portions 34 and 35 such that the slide portions 34 and 35 can move along the axis of the syringe.

The outer tube fixing portion 31 includes input arms 40 and 41 having first ends rotatably coupled to fixed supports 38 and 39 that are provided at the slide guides 36 and 37, respectively, and a press portion 43 that is coupled to second ends of the input arms 40 and 41. The press portion 43 according to the present embodiment 1 has a shaft-like portion 43a that has ends fixed to the input arms 40 and 41, respectively, and a pad-like portion 43b that is provided at a center of the shaft-like portion 43a and has certain elasticity. The outer tube fixing portion 31 has transmission arms 48 and 49 that have first ends rotatably coupled to first supports 44 and 45 respectively provided at intermediate positions of the input arms 40 and 41, and second ends rotatably coupled to second supports 46 and 47 respectively provided at the slide portions 34 and 35, which are located in front of the slide guides 36 and 37, respectively. The syringe mount portion 51 is configured by the slide portions 34 and 35, the slide guides 36 and 37, the input arms 40 and 41, and the transmission arms 48 and 49. The syringe mount portion 51 is provided between paired link mechanisms that operate in synchronization with each other. In other words, the paired link mechanisms are provided at the respective ends of the syringe mount portion 51.

Figure 5:
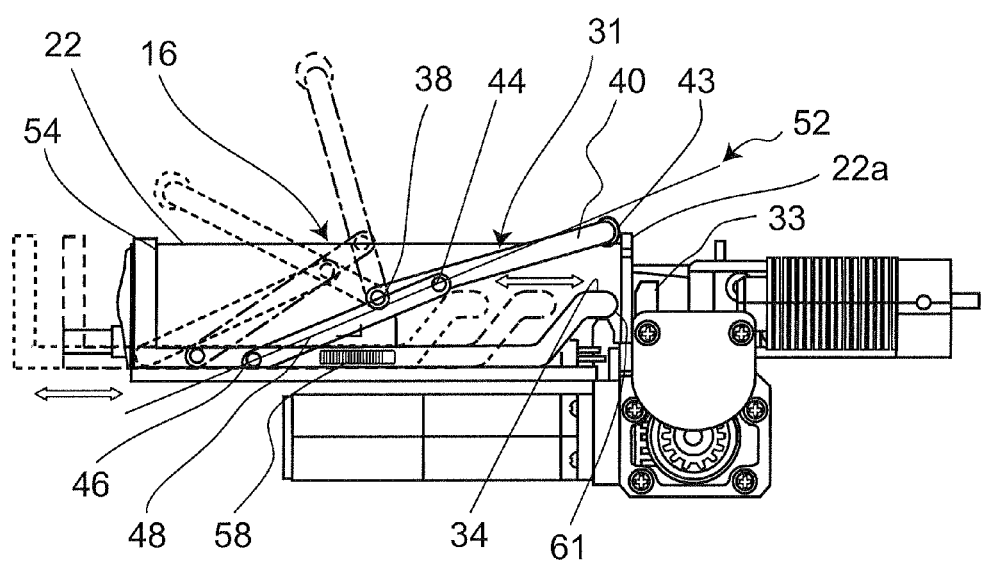
FIG. 5 is a side view showing the main portion of the syringe drive device according to the embodiment 1.

As shown in FIG. 5, there is provided, between the slide portions 34 and 35 and the slide guides 36 and 37, bias springs 58 serving as bias members that elastically bias the slide portions 34 and 35 so as to be away from the flange catcher 33 (forward). There is also provided, at front ends of the slide guides 34 and 35, which are located in front of the slide guides 34 and 35, an outer tube distal end holder 54 that is a coupled semicircular member in the present embodiment. In the present embodiment, there is further provided a rubber member serving as an elastic body, at a contact portion 61 that is located at the rear distal ends of the slide portions 34 and 35 and faces the flange catcher 33.

When the slide portions 34 and 35 are linearly moved in conjunction with the rotation of the input arms 40 and 41, the outer tube fixing portion 31 can be switched between the attached state shown in FIG. 3 and the released state shown in FIG. 4.

In order to attach the syringe 16 to the syringe drive device 15, when the outer tube fixing portion 31 is in the released state shown in FIG. 4, the operator moves downward the outer tube 22 of the syringe 16 into the syringe mount portion 51 such that the outer tube 22 passes between the input arms 40 and 41 and the press portion 43. When the outer tube 22 is mounted in the syringe mount portion 51, the flange 22a of the outer tube 22 is located between the slide portions 34 and 35 and the flange catcher 33. Further, upon mounting the outer tube 22 in the syringe mount portion 51, the brim 20 of the plunger 17 is inserted into the accommodating portion 21a of the plunger holder 21. Subsequently, the operator pinches the press portion 43 and rotates the input arms 40 and 41 about the fixed supports 38 and 39 so as to come close to the flange 22a of the syringe 16, respectively. When the input arms 40 and 41 reach the positions in the attached state shown in FIG. 3, the syringe 16 is fixed to the outer tube fixing portion 31.

In order to detach the syringe 16 from the syringe drive device 15, the operator rotates the input arms 40 and 41, which are located in the attached state shown in FIG. 5, about the fixed supports 38 and 39 so as to move away from the first flange 22a of the syringe 22. When the input arms 40 and 41 are brought into the released state shown in FIG. 4, the outer tube 22 of the syringe 16 is lifted upward from the syringe mount portion 51, and the brim 20 of the plunger 17 can be extracted from the accommodating portion 21a of the plunger holder 21.

Described next is laterally observed two-dimensional motion of the link mechanisms with reference to the side view of FIG. 5 showing the main portion of the syringe drive device 15. In FIG. 5, dotted lines shape the link mechanisms in the released state (FIG. 4), dashed lines shape the link mechanisms during deformation, and solid lines shape the link mechanisms in the attached state (FIG. 5), respectively. In the following description on the link mechanisms, the upward direction is along an arrow 50 indicated in FIG. 1, in which the syringe 16 is placed when viewed from the grip portion 18, and which is opposite to the grip portion 18 when viewed from the syringe 16.

One of the link mechanisms is configured by the input arm 40, the transmission arm 48, the slide portion 34, the fixed support 38, the first support 44, the second support 46, and the slide guide 36. The following description mainly refers to the link mechanism including the slide portion 34. It is noted that the other one of the link mechanisms including the slide portion 35 is configured similarly to the link mechanism including the slide portion 34. More specifically, the link mechanism including the slide portion 35 is configured symmetrically with the link mechanism including the slide portion 34, by the input arm 41, the transmission arm 49, the slide portion 35, the fixed support 39, the first support 45, the second support 47, and the slide guide 37. In this link mechanism, the input arm 41 is connected to the input arm 40 with the press portion 43 provided therebetween, so as to be coupled with the link mechanism that is configured by the input arm 40, the transmission arm 48, the slide portion 34, the fixed support 38, the first support 44, the second support 46, and the slide guide 36. In this configuration, the two link mechanisms operate in synchronization with each other.

In the released state, as indicated by the dotted lines in FIG. 5, the input arm 40 is tilted forward with respect to the fixed support 38 (toward the injection port of the syringe 16) so as not to disturb the syringe 16 to be inserted into and extracted from the syringe mount portion 51. The slide portion 34 is also located such that the outer tube distal end holder 54 is not in contact with the side portion of the outer tube 22. In this state, the outer tube 22 of the syringe 16 is mounted in the syringe mount portion 51 as described earlier, and the brim 20 of the plunger 17 is inserted into the accommodating portion 21a of the plunger holder 21.

Subsequently, in order to bring the outer tube fixing portion 31 into the attached state, the press portion 43 is pinched and the input arm 40 is rotated about the fixed support 38 so as to come close to the flange 22a of the syringe 16. Due to the rotation of the input arm 40, the slide portion 34 is pulled by the input arm 40 by way of the transmission arm 48. The slide portion 34 is guided by the slide guide 36 and linearly moves backward so as to come close to the flange catcher 33.

The following description refers to the transition of the link mechanism in accordance with the rotation of the input arm 40 toward the flange 22a. While the input arm 40 transitions from the posture indicated by the dashed lines into the posture indicated by the solid lines in FIG. 5, the first support 44, the fixed support 38, and the second support 46 are aligned on one straight line (in a state where the fixed support 38 is positioned on an inflection line 52 that connects the fixed support 38 and the second support 46). In this state where the first support 44, the fixed support 38, and the second support 46 are aligned on one straight line, the slide portion 34 is brought closest to the flange catcher 33.

From this state until the press portion 43 is brought into contact with the outer tube 22, the input arm 40 is further rotated. When the press portion 43 is in contact with the outer tube 22 mounted in the syringe mount portion 51, the fixed support 38 is located above the straight line (inflection line 52) that connects the first support 44 and the second support 46. In this case, the slide portion 34 is slightly moved forward so as to be away from the flange catcher 33, and the flange 22a is held between the flange catcher 33 and the slide portion 34. The press portion 43 is moved downward from the state where the first support 44, the fixed support 38, and the second support 46 are aligned on the straight line, and presses the outer tube 22 from upward so that the outer tube 22 is held between the bottom portion and the press portion 43. In this manner, the outer tube 22 is fixed to the outer tube fixing portion 31.

When the input arm 40 is rotated so as to move away from the flange 22a in the attached state, the press portion 43 initially moves upward so as to be away from the outer tube 22. When the press portion 43 moves upward from the state where the first support 44, the fixed support 38, and the second support 46 are aligned on the straight line, the slide portion 34 moves away from the flange 22a of the outer tube 22.

In the syringe drive device 15 according to the present embodiment 1, the outer tube fixing portion 31 is designed such that the fixed support 38 is located above the inflection line 52 when the press portion 43 is in contact with the outer tube 22. In this configuration, the syringe drive device 15 can stably fix the syringe 16 in the attached state.

Figure 6:
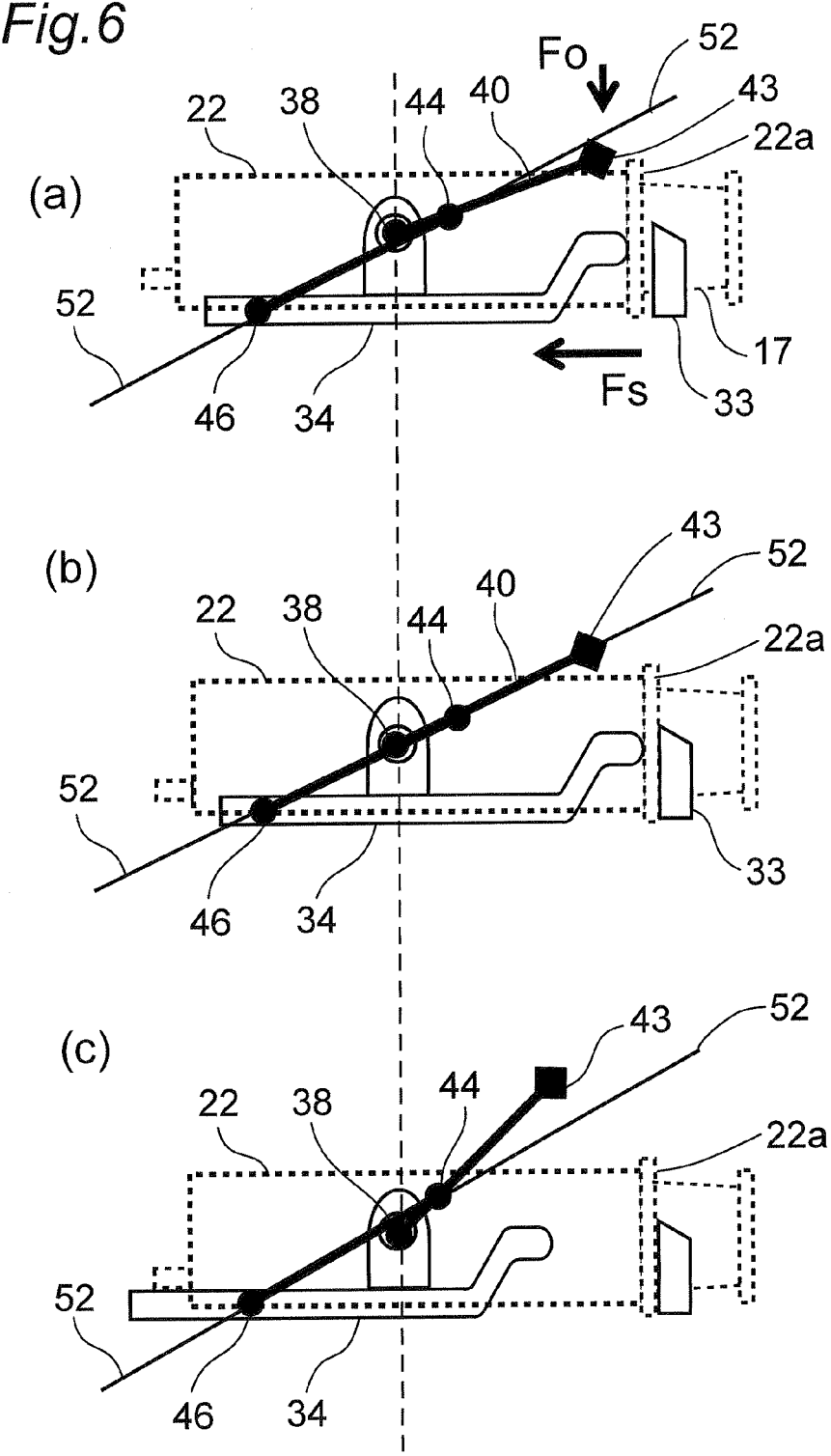
FIGS. 6(a) to 6(c) are views of a link mechanism according to the embodiment 1.

More specifically, as shown in the schematic view of the link mechanism in the attached state in FIG. 6(a), when the outer tube 22 is moved forward with respect to the syringe 16 together with the plunger 17 being pushed, the slide portion 34 is brought into contact with the flange 22a to stop the movement of the outer tube 22. A force Fs of the outer tube 22 to push the slide portion 34 forward with respect to the syringe 16 is converted by the link mechanism into a force Fo of the press portion 43 to press the outer tube 22. In other words, when the plunger 17 is pushed, the press portion 43 presses the outer tube 22 from upward, so that the outer tube 22 can be fixed stably.

In addition, it is easy to bring the syringe 16 in the attached state into the released state. In the attached state shown in FIG. 6(a), when the input arm 40 or the press portion 43 is pinched upward, the press portion 43 starts to move away from the outer tube 22.

When the press portion 43 is pinched upward, the slide portion 34 moves backward (toward the flange catcher 33) in conjunction therewith. In this case, there needs a small force for pushing the flange 22a toward the flange catcher 33. The present embodiment 1 adopts a configuration in which the force for pinching upward the press portion 43 is smaller than the force for moving the slide portion 34. More specifically, by setting the fixed support 38 as a fulcrum, the press portion 43 as a power point, and the first support 44 as a point of action, respectively, the force for pinching upward the press portion 43 is reduced according to the principle of leverage.

Until the link mechanism is brought into the state at the inflection point (where the fixed support 38 is positioned on the inflection line 52) as shown in FIG. 6(b), there needs the force for pushing the flange 22a toward the flange catcher 33. When the link mechanism transitions beyond the state at the inflection point and the fixed support is located below the inflection line as shown in FIG. 6(c), the slide portion 34, which has been moving backward, starts to move forward. Thus, the slide portion 34 no longer pushes the flange 22a, and the force for pinching upward the press portion 43 is also reduced.

In this configuration, it is possible to provide the syringe drive device that can stably fix the syringe while the syringe is easily attached and detached.

In the syringe drive device 15 according to the present embodiment 1, after pressing the lower portion of the operation switch 19 to push the plunger 17, the operation switch 19 is returned to the flat state to stop the movement of the plunger holder 21. When the syringe 16 is subsequently detached from the syringe drive device 15, the syringe 16 will not be held but can be detached easily. This feature is detailed below.

In the case of a conventional infusion solution transfer device 1 (syringe drive device) shown in FIGS. 22(a) and 22(b), when the plunger 4 is pushed by the plunger holder 3 and is then stopped, the syringe 5 is held between the press surface 12 of the plunger holder 3 and the flange front surface support portion 9. Therefore, it has been difficult to detach the syringe 5 from the infusion solution transfer device 1. Meanwhile, as shown in FIG. 5, the syringe drive device 15 according to the present embodiment 1 includes the outer tube fixing portion 31 that fixes the outer tube 22 of the syringe 16. When the outer tube fixing portion 31 transitions from the fixed state into the released state, the slide portion 34 initially moves slightly close to the flange catcher 33, and then moves forward so as to be away from the flange catcher 33. In other words, upon detaching the syringe 16, the slide portion 34 moves forward so as to be away from the flange 22a. Accordingly, the syringe 16 is not kept being held between the plunger holder 21 and the slide portion 34. Therefore, even in a case where the plunger 17 is pushed by the plunger holder 21 and then stops, it is possible to easily detach the syringe 16.

The feature of not causing holding will be described in more detail with reference to FIGS. 7(a) and 7(b). Assume that, upon detaching the syringe 16, as shown in FIG. 7(a), not the slide portions 34 and 35 located in front of the flange 22a of the outer tube 22, but the flange catcher 33 located behind (at the rear-end side of) the flange 22a, moves away from the flange 22a. In this case, as indicated by an arrow P12, the slide portion 34 and 35 inhibit the flange 22a from moving forward against a force (indicated by an arrow P11) of the plunger 17 to push forward the outer tube 22. As a result, the syringe 16 is held. To the contrary, according to the present embodiment 1, it is not the flange catcher 33 located behind the flange 22a but each of the slide portions 34 and 35 located in front of (at a front-end side of) the flange 22a that moves away from the flange 22a of the outer tube 22 when the syringe 16 is detached. Thus, as shown in FIG. 7(b), neither the slide portions 34 and 35 that have already moved away nor the flange catcher 33 located behind the flange 22a resists the force (indicated by the arrow P11) of the plunger 17 to push forward the outer tube 22. As a result, the syringe 16 is not held.

Further, as described earlier, the bias spring 58 (see FIG. 5) serving as an elastic body is provided between the slide portion 34 and the slide guide 36 and biases the slide portion 34 so as to be away from the flange catcher 33. In this configuration, the syringe 16 can be more reliably fixed to the outer tube fixing portion. Even in a case where there is acting no force for pushing the plunger 17, the bias spring 58 generates a force for pushing forward the slide portion 34. As a result, the press portion 43 presses downward the outer tube 22 by way of the transmission arm 48 and the input arm 40. In other words, the press portion 43 constantly presses the outer tube 22 with use of the force of the bias spring 58 so as to fix the syringe 16.

As described earlier, the syringe drive device 15 according to the present embodiment 1 can stably fix the syringe 16, while the syringe 16 can be easily attached and detached.

Further, as described earlier, the outer tube distal end holder 54 is provided to the slide portion 34 in front of the slide guide 36. The outer tube distal end holder 54 holds the outer tube 22 of the syringe 16, which can be therefore fixed stably. This feature is detailed below.

Figure 8:
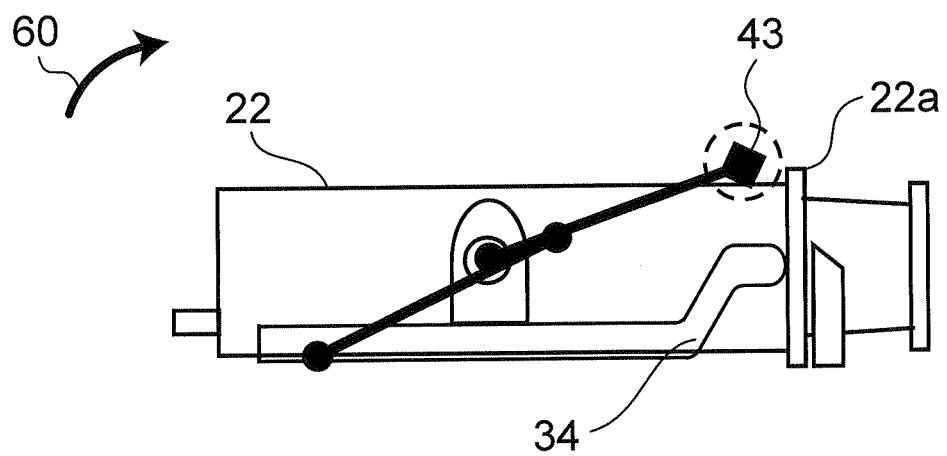
FIG. 8 is a side schematic view of an outer tube fixing portion, illustrating tilt rotation.

Assume that, as shown in FIG. 8, the outer tube 22 is fixed simply by holding the flange 22a between the flange catcher 33 and the slide portion 34 and pressing the flange and its vicinity of the outer tube 22 by the press portion 43. In this case, the front portion of the outer tube 22 is not fixed, and thus tilt rotation in the direction indicated by an arrow 60 may occur to the front portion of the syringe 16.

To the contrary, according to the present embodiment 1, as shown in FIG. 5, the front portion of the outer tube 22 is held by the outer tube distal end holder 54, so that the both ends of the outer tube 22 can be fixed. As a result, it is possible to stably fix the outer tube 22 of the syringe 16. Even in the case where a force for causing tilt rotation is applied to the outer tube 22, such tilt rotation can be suppressed because the outer tube 22 is pressed at two positions by the press portion 43 and the outer tube distal end holder 54.

Further, the outer tube distal end holder 54 is provided at the slide portion 34. As shown in FIG. 5, the outer tube distal end holder 54 is located at a position to hold the outer tube 22 when the outer tube fixing portion 31 is in the attached state, while the outer tube distal end holder 54 is located away from the outer tube 22 when the outer tube fixing portion 31 is in the released state. When attaching the syringe 16 to the outer tube fixing portion 31, the outer tube distal end holder 54 in the released state is located away from the syringe mount portion 51. Therefore, the syringe 16 can be attached easily. Assume that the outer tube distal end holder 54 is provided at the rack covers 24 shown in FIG. 1 or any other immovable portion, it is necessary to pass the distal end of the syringe 16 through the outer tube distal end holder 54 when the syringe 16 is attached to the outer tube fixing portion 31. In this case, it may take more time to attach the syringe. In the syringe drive device 15 according to the present embodiment 1, the outer tube distal end holder 54 is provided at the slide portion 34, so that the syringe can be attached easily.

Figure 9:
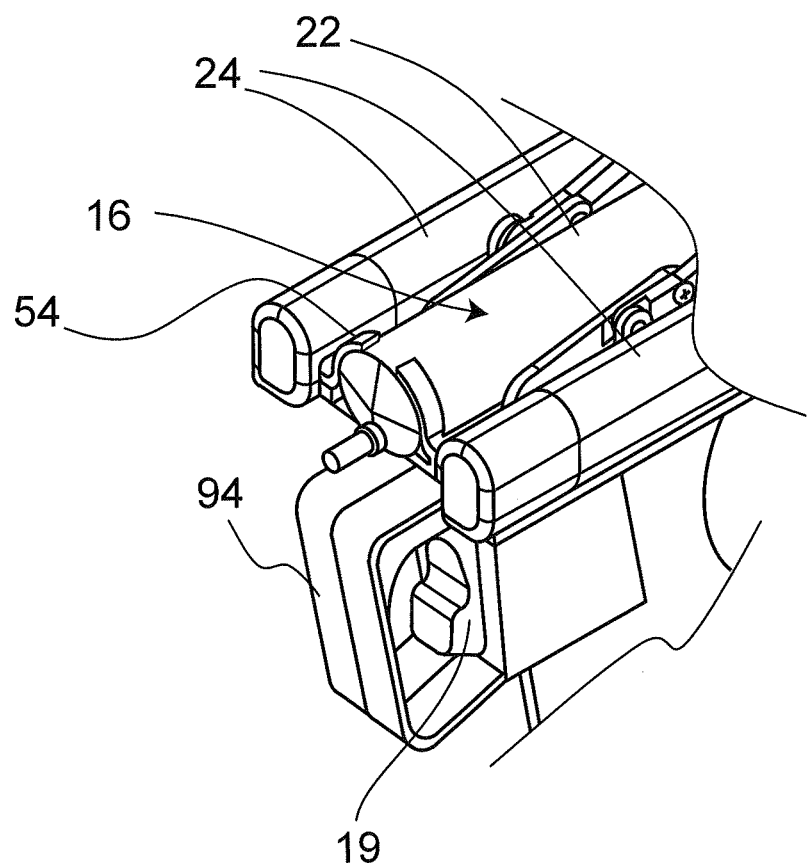
FIG. 9 is a perspective view showing a substitute for an outer tube distal end holder.

In the present embodiment 1, the outer tube distal end holder 54 has a ring shape to connect the two slide portions 34 and 35. Alternatively, the outer tube distal end holder 54 may be in a different shape as long as being capable of suppressing tilt rotation of the outer tube 22. As an example of such an alternative shape, the outer tube distal end holder 54 may be possibly replaced with an outer tube distal end holder 154 having a ring shape with an upper portion being cut off, as shown in FIG. 9. The outer tube distal end holder 154, which has such a ring shape with the upper portion being cut off, does not disturb attaching and detaching the syringe 16 to which distal end the injection needle 90 is attached (see FIG. 21). Therefore, the syringe can be attached and detached more easily.

Figure 10:
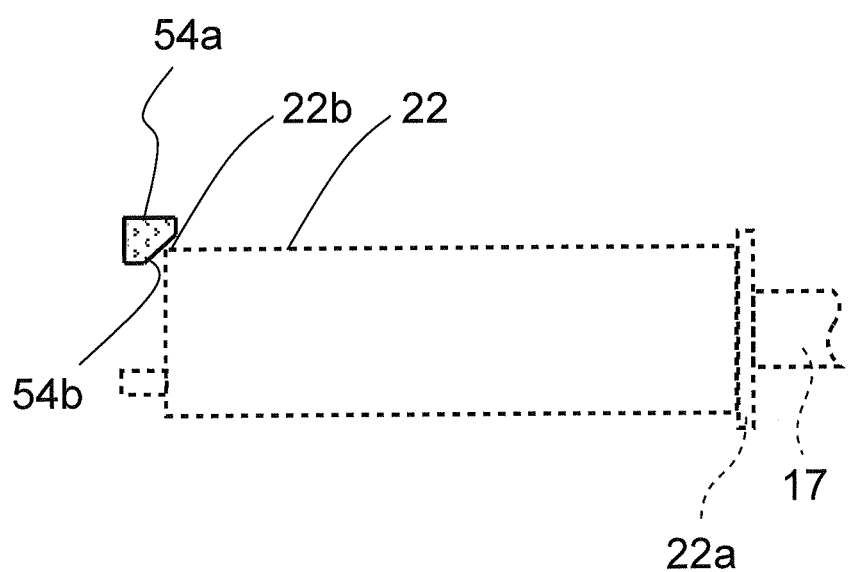
FIG. 10 is a sectional view of another outer tube distal end holder according to the embodiment 1.

Further alternatively, as shown in the sectional view of the outer tube distal end holder in FIG. 10, an outer tube distal end holder 54a may be provided with a tilted surface 54b, so that the tilted surface 54b presses an upper end corner 22b of the outer tube 22 upon attaching the syringe. When the tilted surface 54b presses the corner 22b in this manner, tilt rotation can be suppressed, and the outer tube can be firmly fixed also in the direction of the axis of the syringe.

As described earlier, the rubber member serving as an elastic body is provided at the contact portion 61 of the slide portions 34 and 35, which faces the flange catcher 33. Therefore, the flange 22a can be fixed more stably. This feature is detailed below.

As shown in FIG. 6(c), when the outer tube fixing portion 31 is in the released state, the contact portion 61 of the slide portion 34 and the flange catcher 33 forms a gap that is slightly wider than the thickness of the flange 22a. When the input arm 40 is rotated in this state toward the flange 22a to reach the state at the inflection point shown in FIG. 6(b), the gap between the contact portion 61 of the slide portion 34 and the flange catcher 33 is minimized. When the outer tube fixing portion 31 is in the attached state as shown in FIG. 6(a), the gap between the slide portion 34 and the flange catcher 33 is slightly widened in comparison to the state at the inflection point.

Assuming that the contact portion 61 of the slide portion 34 is rigid, the gap of the minimum size (the gap in the state at the inflection point) between the contact portion 61 and the flange catcher 33 cannot be set to be narrower than the thickness of the flange 22a. When the outer tube fixing portion 31 transitions into the attached state and the gap between the slide portion 34 and the flange catcher 33 is slightly widened in comparison to the minimum size, the gap between the slide portion 34 and the flange catcher 33 is larger than the thickness of the flange 22. As a result, it is impossible to stably hold the flange 22a between the slide portion 34 and the flange catcher 33.

To the contrary, according to the present embodiment 1, the contact portion 61 is configured by the rubber member. It is thus possible to set the gap of the minimum size between the slide portion 34 and the flange catcher 33 in the state at the inflection point so as to be smaller than the thickness of the flange 22a. More specifically, because the contact portion 61 is elastically compressed, the slide portion 34 can move close to the flange catcher 33 until the gap between the flange catcher 33 and the slide portion 34 is made smaller than the thickness of the flange 22. In this configuration, even when the outer tube fixing portion 31 transitions into the attached state and the gap between the contact portion 61 and the flange catcher 33 is made slightly larger than the minimum size, the flange 22a is elastically held between the flange catcher 33 and the contact portion 61. Therefore, the flange can be reliably held with no gap formed therebetween.

In place of the contact portion 61, or in addition to the contact portion 61, the portion of the flange catcher 33 to be in contact with the flange 22a may be configured by a rubber member.

As shown in FIGS. 3 and 4, the syringe drive device 15 according to the present embodiment 1 includes a push-up portion 63 at the bottom of the outer tube fixing portion 31 (on the bottom surface of the syringe mount portion 51). The push-up portion 63 moves upward and downward in accordance with the positions of the slide portions 34 and 35. When the slide portions 34 and 35 are located in the vicinity of the flange catcher 33, the push-up portion 63 holds the syringe 16 at the mount position. When the slide portions 34 and 35 are away from the flange catcher 33, the push-up portion 63 pushes upward the syringe so as to be located above the bottom of the outer tube fixing portion 31 (the bottom surface of the syringe mount portion 51). The push-up portion 63 thus provided allows the attached syringe 16 to be easily extracted.

More specifically, when the outer tube fixing portion 31 is in the released state, the push-up portion 63 pushes upward the syringe 16, which is thus slightly disengaged upward. In this state, the operator can easily pinch the syringe 16. Particularly in a case where the rack covers 24 and the like are located on the respective sides of the syringe mount portion 51, the rack covers 24 may disturb pinching and detaching the syringe 16. In this case, provision of the push-up portion 63 facilitates detaching the syringe 16.

The push-up portion 63 shown in FIGS. 3 and 4 is configured by a movable plate 64 and projections 65 that are provided on inner side surfaces of the slide portions, respectively. Description will be given with reference to FIGS. 11(a) and 11(b), which show the relationship between the slide portion 34 and the push-up portion 63. FIG. 11(a) is a side view showing the relationship between the slide portion 34 and the movable plate 64 when the outer tube fixing portion 31 is in the attached state. The movable plate 64 has a rear end rotatably coupled, at a movable plate support 67, to the main body 27 of the syringe drive device 15 (see FIG. 1). The movable plate 64 and a bottom plate portion 66 configure the bottom surface of the syringe mount portion 51. The movable plate 64 is rotatable about the movable plate support 67 between the posture to be made flat with respect to the bottom plate portion 66 (FIG. 11(a)) and the posture with a front end being lifted obliquely upward.

FIG. 11(b) is a side view showing the relationship between the slide portion 34 and the movable plate 64 when the outer tube fixing portion 31 is in the released state. When the outer tube fixing portion 31 transitions from the attached state into the released state, the slide portion 34 moves away from the flange catcher 33 (to the left in FIGS. 11(a) and 11(b)). In this case, the projection 65 provided at the slide portion 34 moves to be located below the movable plate 64, which is therefore lifted obliquely upward about the movable plate support 67. To the contrary, when the outer tube fixing portion 31 transitions from the released state into the attached state, the slide portion 34 moves close to the flange catcher 33 (to the right in FIGS. 11(a) and 11(b)). In this case, the projection 65 provided onto the slide portion 34 is not located below the movable plate 64, which is therefore made flat with respect to the movable plate 64.

There may be provided an idle running section t, in which, during the transition from the released state shown in FIG. 11(b) into the attached state shown in FIG. 11(a), after the movable plate 64 having lifted obliquely upward is made flat with respect to the bottom plate portion 66, the slide portion 34 can move while being kept flat with respect to the bottom plate portion 66. When the movable plate 64 is made flat with respect to the bottom plate portion 66, the outer tube 22 is made in parallel with the syringe mount portion 51. By providing the idle running section t, the outer tube 22 can be made in parallel with the syringe mount portion 51 before the slide portion 34 starts to press and hold the front surface of the flange 22a. The flange 22a is therefore prevented from being held while the flange 22a is tilted. In this manner, it is possible to avoid holding the syringe 16 in an inappropriate state.

Particularly in the process of the transition from the syringe released state into the attached state, the widths of the idle running section t and the outer tube distal end holder 54 may be set such that the front end surface of the outer tube distal end holder 54 attached to the slide portion 34 reaches the distal end of the outer tube of the syringe 16 before entering the idle running section t (while the outer tube 22 of the syringe 16 is still tilted). Because the outer tube 22 of the syringe 16 is tilted, the distal end of the outer tube is located at a low level. Accordingly, the distal end of the outer tube can be stably located below the outer tube distal end holder 54. As a result, the outer tube distal end holder 54 is prevented from being caught by the distal end of the outer tube of the syringe. Therefore, the syringe can be attached more smoothly.

Embodiment 2

In a syringe drive device according to the present embodiment 2, the press portion includes a thickness adjuster that changes the distance from a syringe mounted on the outer tube fixing portion 31.

As shown in FIG. 5, in the syringe drive device 15 in the attached state, the distance between the slide portion 34 and the flange catcher 33 is determined by the degree of tilt of the input arm 40 due to the linking structure. The attached state is established when the press portion 43 coupled with the input arm 40 is in contact with the outer tube 22. Accordingly, the degree of tilt of the input arm 40 is varied depending on the outer diameter of the outer tube 22. Accordingly, the distance between the slide portion 34 and the flange catcher 33 is determined by the outer diameter of the outer tube 22. There will be no problem if the outer diameters of syringes 16 to be used in the syringe drive device 15 are all the same. However, if the syringe 16 of a different outer diameter is used, the distance between the slide portion 34 and the flange catcher 33 is changed, with a result that the flange 22a may not be fixed between the slide portion 34 and the flange catcher 33.

According to the present embodiment 2, there is provided the thickness adjuster that changes the thickness of the press portion 43 shown in FIG. 5. In this configuration, even if the syringe 16 has a different outer diameter, the distance between the slide portion 34 and the flange catcher 33 can be kept constant, so that the syringe 16 can be fixed stably.

FIG. 12(a) is a side schematic view in a state where the press portion being used is thin, while FIG. 12(b) is a side schematic view in a state where the press portion being used is thick.

FIGS. 12(a) and 12(b) each show the state where the syringe 16 is attached onto the outer tube fixing portion 31. The press portion 43 includes a coupling shaft 73 that has ends respectively fixed to the input arms 40 and 41, and a thickness adjuster 71 that is provided as a pad and rotatably attached to the coupling shaft 73 at the longitudinal center or the vicinity thereof. The thickness adjuster 71 has a shape of an ellipsoidal cylinder and is made in contact with aside surface 72 of the outer tube 22. The thickness adjuster is rotatable about an axis thereof with respect to the coupling shaft 73. The thickness adjuster 71 is not freely rotatable with respect to the coupling shaft 73, but can take a posture such as that shown in FIG. 12(a) or 12(b) so as to be positioned at a rotation angle with respect to the coupling shaft 73.

When the syringe 16 of the standard type is used in the syringe drive device 15, as shown in FIG. 12(a), the peripheral surface of the minor axis of the ellipse of the thickness adjuster 71 is brought into contact with the side surface 72 of the outer tube 22. In other words, the press portion 43 is used with the thickness being reduced.

When the syringe 16 is of a small type and has an outer diameter smaller than that of the syringe 16 of the standard type, if the press portion 43 is used without increasing the thickness thereof, the input arm 40 is remarkably tilted. In this case, the distance between the slide portion 34 and the flange catcher 33 is made too large, with a result that the syringe 16 cannot be fixed stably. Therefore, in the case of the syringe 16 of such a small type, as shown in FIG. 12(b), the peripheral surface of the major axis of the ellipse of the thickness adjuster 71 is brought into contact with the side surface 72 of the outer tube 22. The press portion 43 is thus used with the thickness being increased. In this manner, by changing the thickness of the press portion 43, the degree of tilt of the input arm 40 does not need to be changed even when the syringe to be used is of a small size with the outer tube 22 having a small outer.

Figure 13:
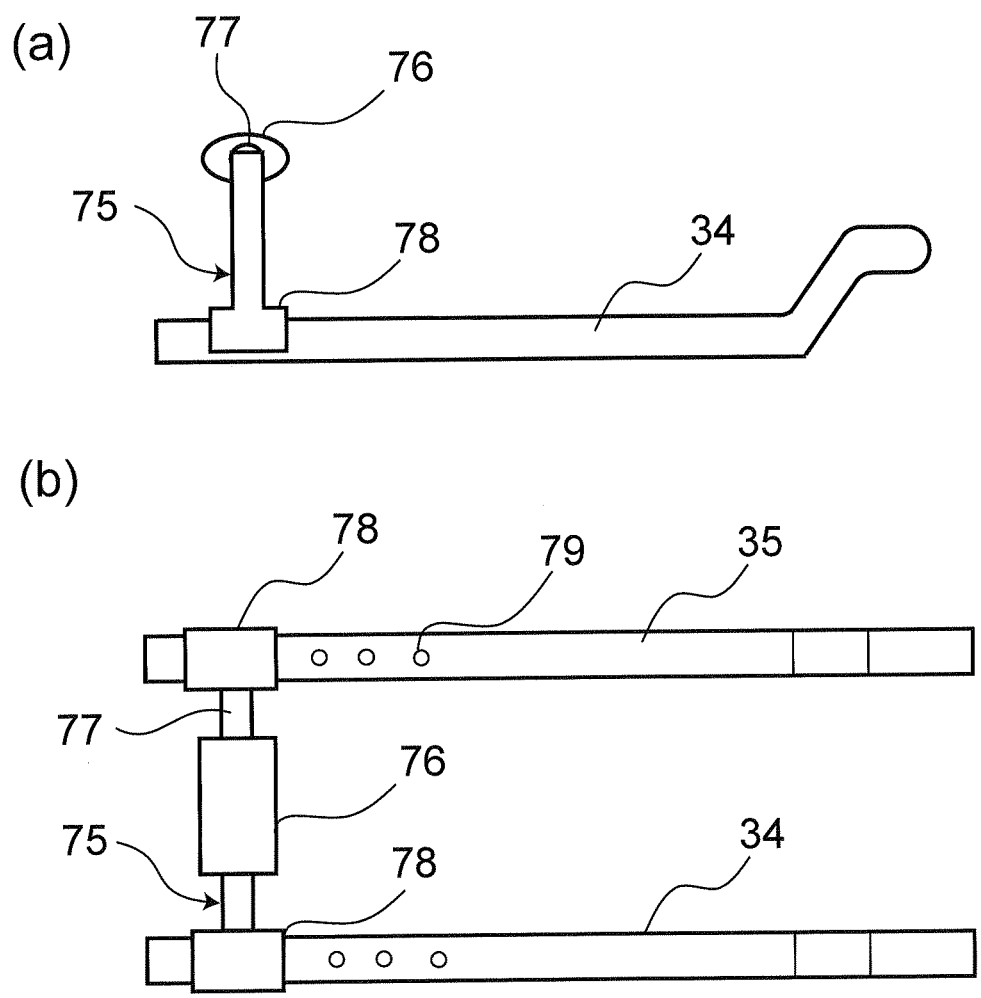
FIGS. 13(a) and 13(b) are views showing a slide portion that has a movable outer tube distal end holder according to the embodiment 2.

As shown in FIGS. 13(a) and 13(b), in the syringe drive device according to the present embodiment 2, an outer tube distal end holder 75 is also provided with a rotatable thickness adjuster 76 having an ellipsoidal shape, so that the syringe 16 having a different outer diameter can be fixed stably. The outer tube distal end holder 75 according to the present embodiment 2 includes a coupling shaft 77 that has ends fixed to pedestals 78, 78 attached to the slide portions 34 and 35, respectively, and the thickness adjuster 76 that has a shape of an ellipsoidal cylinder and is rotatably attached to the coupling shaft 77 at the longitudinal center or the vicinity thereof so as to be positioned at a rotation angle with respect to the coupling shaft 77. By adjusting the position in terms of the rotation angle of the thickness adjuster 76, similarly to the case of the thickness adjuster 73, the thickness of the outer tube distal end holder 75 can be adjusted in accordance with the outer diameter of the syringe 16.

The pedestals 78 supporting the coupling shaft 77 moves forward or backward on the slide portions 34 and 35 to change positions fixed to the slide portions 34 and 35, respectively. More specifically, when convex portions (not shown) provided at the pedestals 78 of the outer tube distal end holder 75 are inserted into any one of pairs of coupling holes 79 provided respectively in the slide portions 34 and 35, it is possible to adjust the positions of the outer tube distal end holder 75 in the forward and backward directions of the slide portions 34 and 35. Accordingly, the outer tube distal end holder 75 can adapt to the syringes 16 having different lengths in the axial direction. More specifically, when the syringe 16 is short, the pedestals 78 are positioned close to the rear ends of the slide portions 34 and 35, respectively. On the other hand, when the syringe 16 is long, the pedestals 78 are positioned close to the front ends of the slide portions 34 and 35, respectively. In this manner, the distal end of the outer tube 22 can be reliably held by the outer tube distal end holder 75.

Figure 14:
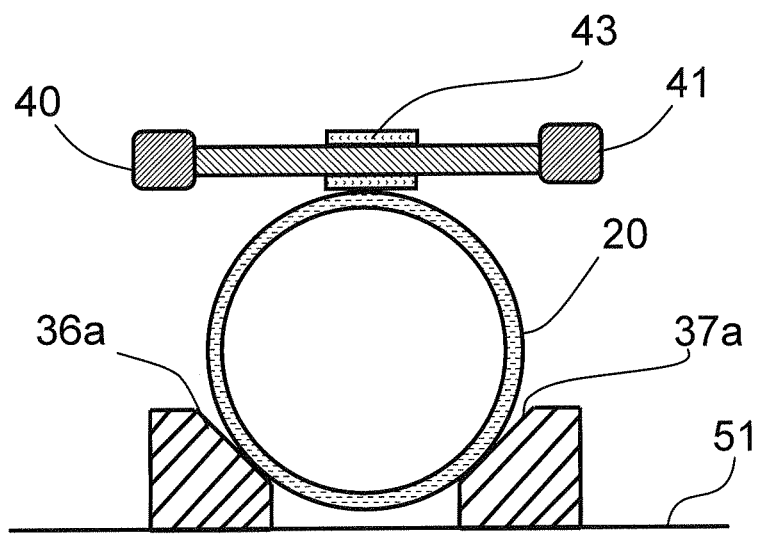
FIG. 14 is a sectional view of the outer tube fixing portion according to the embodiment 2.

The syringe mount portion 51 of the syringe drive device according to the present embodiment 2 supports the outer tube 22 from below. However, in the attached state, the outer tube 22 may be in contact with the syringe mount portion 51 at a portion other than the bottom plate portion 66 and the movable plate 64 that configure the bottom surface of the syringe mount portion 51. For example, as in the sectional view of FIG. 14 showing the outer tube fixing portion 31, the slide guides 36 and 37 may have inner side surfaces 36a and 37a that are tilted, so that the outer tube 22 is supported from below by the inner side surfaces 36a and 37a. Because the outer tube 22 is supported from below by the inner side surfaces 36a and 37a, it is possible to fix the outer tube 22 to the outer tube fixing portion 31 at the center thereof, even if the outer tube 22 of the syringe 16 has a different outer diameter.

Embodiment 3

A syringe drive device according to the present embodiment 3 is characterized in that the input arms are provided with lock portions to be coupled with the slide portions. In such a case where the lock portions are provided, the input arms are fixed reliably, so that the syringe can be fixed more stably.

Figure 15:
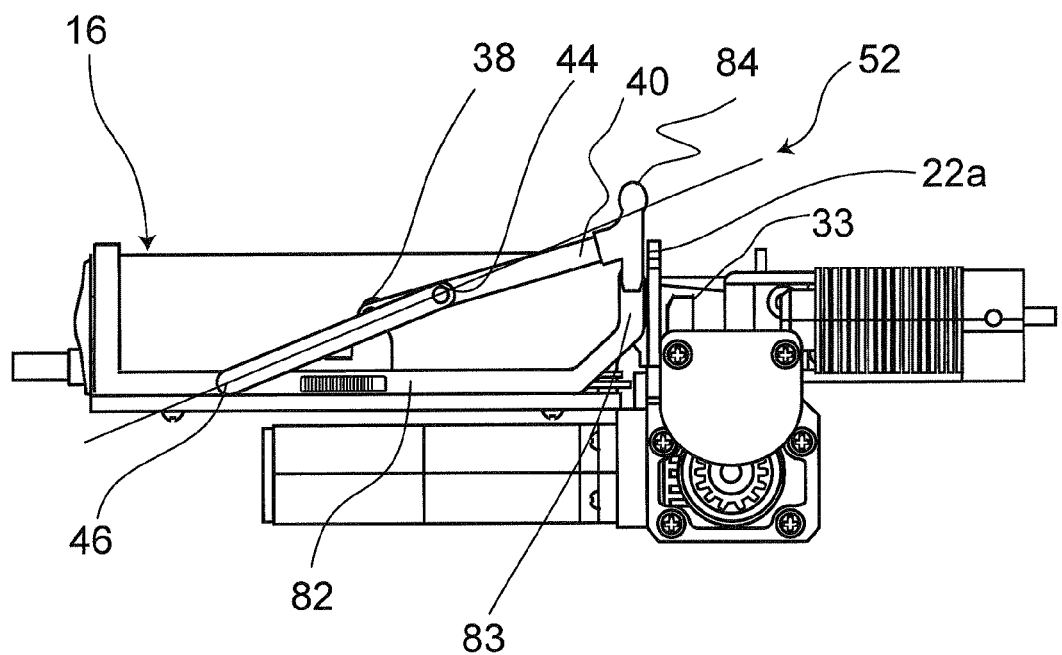
FIG. 15 is a side view showing a main portion of a syringe drive device according to an embodiment 3 of the present invention.

FIG. 15 is a side view showing a main portion of the syringe drive device in the attached state. A slide portion 82 is shaped so as to be bent upward at a portion facing the flange catcher 33. The slide portion 82 and the flange 22a are in contact with each other at a contact portion 83, and an upper position of the contact portion 83 is coupled with a lock portion 84 that is provided at one end of the input arm 40.

Figure 16:
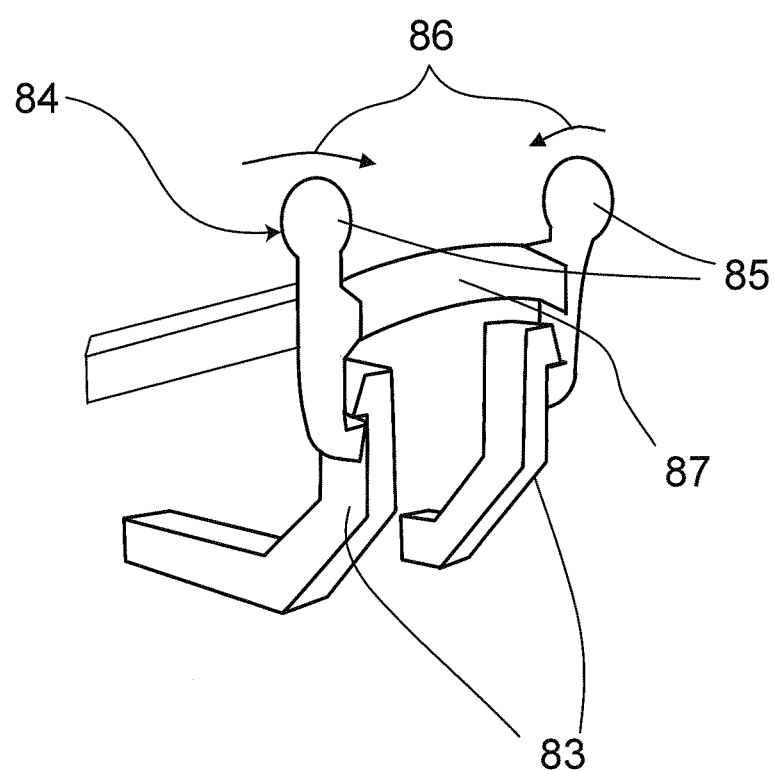
FIG. 16 is a perspective view of a lock portion according to the embodiment 3.

FIG. 16 is a perspective view of the lock portion. The lock portion 84 is locked in FIG. 16. When a knob 85 of the lock portion 84 is pinched and moved along an arrow 86, the locking can be released easily. Moreover, the lock portion 84 has a press portion 87, by which the outer tube 22 of the syringe 16 can be pressed.

When the lock portion 84 is locked with the slide portion 82 as shown in FIG. 15, the fixed support 38 has only to be located above the straight line that connects the first support 44 and the second support 46.

When the lock portion 84 is provided at the input arm 40 in this manner, the syringe drive device according to the present embodiment 3 can fix the syringe 16 more stably.

Embodiment 4

Figure 17:
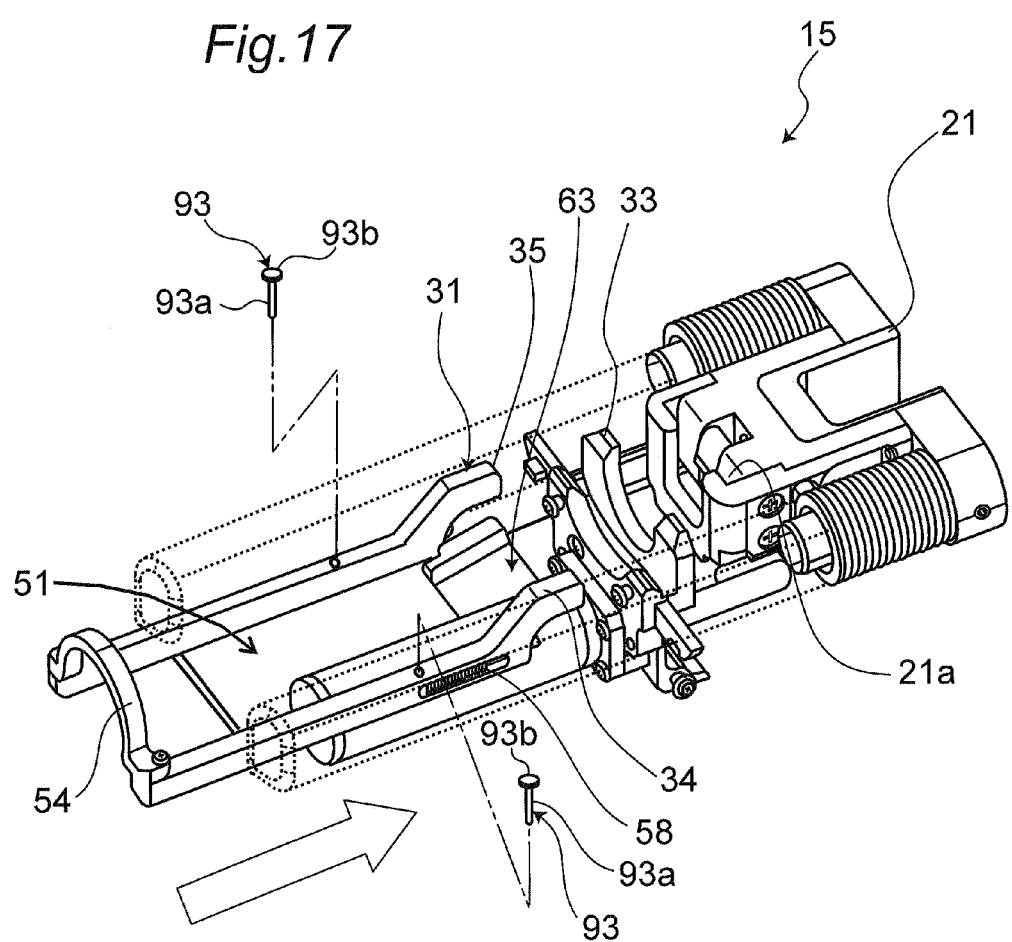
FIG. 17 is a perspective view showing a main portion of a syringe drive device according to an embodiment 4.
Figure 18:
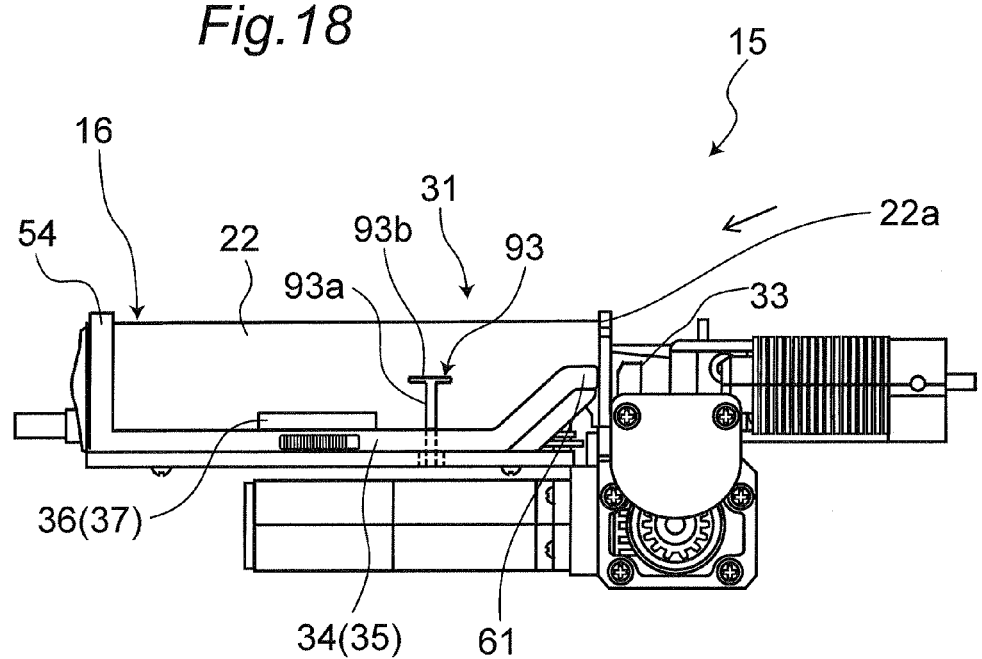
FIG. 18 is a side view of the syringe drive device according to the embodiment 4.
Figure 19:
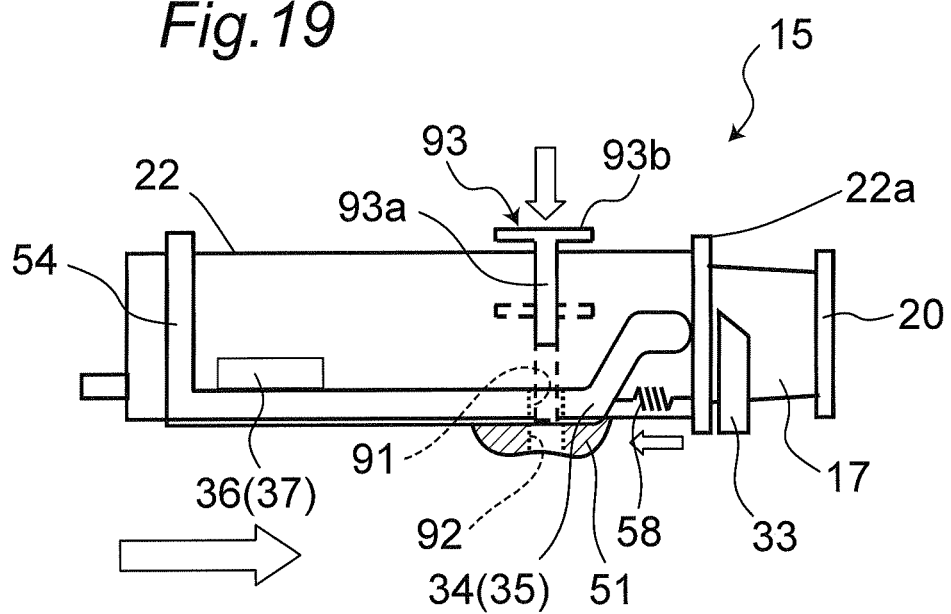
FIG. 19 is a side pattern view of the syringe drive device according to the embodiment 4.

In a syringe drive device 15 according to an embodiment 4 shown in FIGS. 17 to 19, the outer tube fixing portion 31 includes the slide portions 34 and 35, which are guided by the slide guides 36 and 37 and linearly move on the flat syringe mount portion 51 in the longitudinal direction of the syringe 16. The syringe drive device 15 further includes the bias springs 58 that elastically bias the slide portion 34 and 35 so as to be away from the flange catcher 33. Unlike the embodiments 1 to 3, in the outer tube fixing portion 31 according to the present embodiment 4, the slide portions 34 and 35 are driven by the link mechanisms. Accordingly, when the operator pinches the slide portions 34 and 35 to move toward the flange catcher 33, the flange 22a is held between the flange catcher 33 and the slide portions 34 and 35. There is provided a mechanism holding the slide portions 34 and 35 at positions to hold the flange 22a between the flange catcher 33 and the slide portions 34 and 35. This mechanism includes a single through hole 91 that penetrates the slide portions 34 and 35 in the thickness directions thereof, insertion holes 92 that are provided in the syringe mount portion 51 from above for the slide portions 34 and 35 respectively so as to correspond to the through hole 91, and stoppers 93 that have shaft portions 93a to be inserted into the through hole 91 and the insertion holes 92, respectively. The shaft portion 93 of each of the stoppers 93 is provided, at one end, with a knob 93b that is to be held with a hand.

After the slide portions 34 and 35 are manually moved to the positions to hold the flange 22a between the flange catcher 33 and the slide portions 34 and 35, the shaft portions 93a of the stoppers 93 are inserted into the through hole 91 and the insertion holes 92 respectively for the slide portions 34 and 35. Accordingly, the positions of the slide portions 34 and 35 are fixed, and the flange 22a of the outer tube 22 is held while being held between the flange catcher 33 and the slide portions 34 and 35. If the stoppers 93 are extracted from the through hole 91 for the both slide portions 34 and 35, the slide portions 34 and 35 are linearly moved so as to be away from the flange catcher 33 by the bias force of the bias springs 58, so that the flange 22a is released from the held state.

Figure 20:
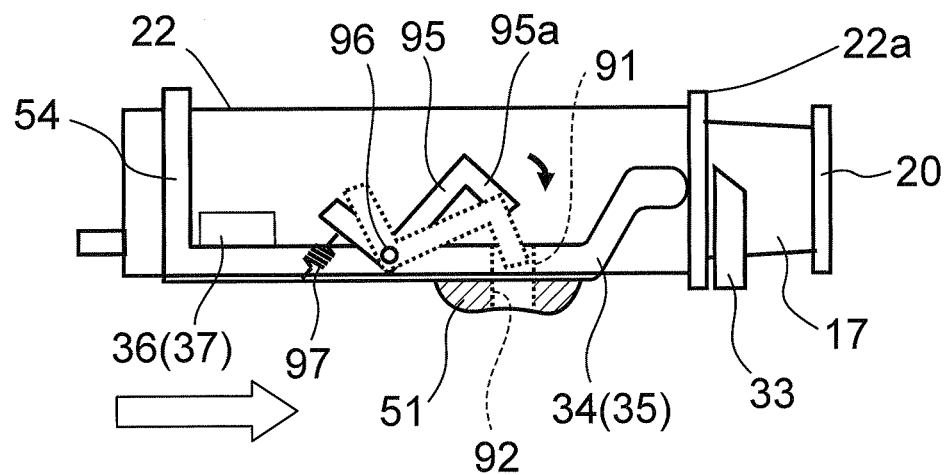
FIG. 20 is a side pattern view of a substitute for a stopper according to the embodiment 4.

FIG. 20 is a view showing another example of the stopper 93 according to the present embodiment 4. The slide portions 34 and 35 are each provided with a stopper 95, which is rotatably attached to corresponding one of the slide portions 34 and 35 at a support 96. The stopper 95 has a first end (front end) coupled to a spring 97, and a second end that configures a shaft portion 95a to be inserted into the through hole 91 and the insertion hole 92. The spring 97 elastically biases the stopper 95 in the direction anticlockwise in the figure about the support 96, so as to achieve the posture indicated by solid lines.

After the slide portions 34 and 35 are manually moved to the positions where the flange 22a is held between the flange catcher 33 and the slide portions 34 and 35, each of the stoppers 95 is pinched with a hand and is rotated clockwise in the figure about the support 96. Accordingly, the shaft portion 93a is inserted into the through hole 91 and the insertion hole 92 for each of the slide portions 34 and 35 (so as to achieve the state indicated by broken lines in the figure). The stoppers 95 are each locked in this posture by a lock mechanism (not shown). When the locking is released, each of the stoppers 95 is rotated clockwise about the support 96 by the bias force of the spring 97, and the shaft portion 93a is extracted from the through hole 91 and the insertion hole 92. The flange 22a is thus released from the held state.

INDUSTRIAL APPLICABILITY

The syringe drive device according to the present invention can stably fix a syringe, while the syringe can be attached and detached easily. The syringe drive device of the present invention is useful for mixing medicinal solutions or the like, in which operation the syringes need to be often exchanged.

The invention claimed is:
1. A syringe drive device comprising:
an outer tube fixing portion for detachably fixing an outer tube of a syringe;
a plunger holder for holding a plunger of the syringe; and
a drive portion for moving the plunger holder along an axis of the syringe;
the plunger being configured to be pushed or pulled along the axis of the syringe by moving the plunger holder;
wherein the outer tube fixing portion includes:
a flange catcher configured to face a rear end side of a flange of the outer tube, the rear end side of the flange being defined as a side farthest from a discharge location of the syringe;
a slide portion configured to be located at a front end side of the flange of the outer tube to hold the flange between the flange catcher and the slide portion, the front end side of the flange being defined as a side closest to the discharge location of the syringe;

a slide guide supporting the slide portion so that the slide portion is slidable along the axis of the syringe; and a slide portion operation mechanism switchable between a first state wherein the slide portion slides along the axis of the syringe, and a second state wherein the slide portion is held at a position to hold the flange of the outer tube between the flange catcher and the slide portion, the slide portion operation mechanism including:

an input arm having a first end rotatably coupled to a fixed support at the slide guide;

a press portion coupled to a second end of the input arm; and a transmission arm having a first end rotatably coupled to a first support at an intermediate position of the input arm, and a second end rotatably coupled to a second support at the slide portion located at a front end side of the slide guide;

wherein the slide portion is configured to move linearly along an axis of the flange in conjunction with rotation of the input arm; and wherein the outer tube fixing portion is configured such that the slide portion is located closest to the flange catcher when the first support, the fixed support, and the second support are aligned in a straight line.

2. The syringe drive device according to claim 1, wherein the outer tube fixing portion is configured such that, when the press portion is in contact with the outer tube of the fixed syringe, the fixed support is located opposite to the syringe with respect to a straight line connecting the first support and the second support.

3. The syringe drive device according to claim 1, wherein the outer tube fixing portion includes two link mechanisms, a first one of the link mechanisms having the slide portion, the slide guide, the input arm, and the transmission arm, and a second one of the link mechanisms having a second slide portion, a second slide guide, a second input arm, and a second transmission arm, wherein a syringe mount portion allowing the outer tube of the syringe to be mounted therein is provided between the two link mechanisms coupled with each other by a shaft of the press portion.

4. The syringe drive device according to claim 3, wherein the press portion has an adjuster for changing a distance from the syringe when the input arm is set at a position where the flange of the outer tube mounted in the syringe mount portion is held between the flange catcher and the slide portion.

5. The syringe drive device according to claim 1, wherein the slide portion has an outer tube distal end holder for holding a distal end of the outer tube of the syringe.

6. The syringe drive device according to claim 1, further comprising:

a bias member elastically biasing the slide member in a direction away from the flange catcher.

7. The syringe drive device according to claim 1, wherein the slide portion has an elastic body partially at a position facing the flange catcher.

8. The syringe drive device according to claim 1, further comprising:

a push-up portion at a bottom of the outer tube fixing portion, the push-up portion being configured to move upward or downward in accordance with movement of the slide portion along the axis of the syringe, and being configured to rotate upward from the bottom when the slide portion moves away from the flange catcher.

9. The syringe drive device according to claim 1, wherein the press portion includes a lock portion detachably coupled to the slide portion located at a position to hold the flange between the flange catcher and the slide portion.

* * * * *